(12) United States Patent
Devries et al.

(10) Patent No.: US 11,311,515 B2
(45) Date of Patent: *Apr. 26, 2022

(54) OXYMETAZOLINE COMPOSITIONS

(71) Applicant: RVL Pharmaceuticals, Inc., Bridgewater, NJ (US)

(72) Inventors: Tina Devries, Bridgewater, NJ (US); David Jacobs, Bernardsville, NJ (US)

(73) Assignee: RVL Pharmaceuticals, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/461,052

(22) Filed: Aug. 30, 2021

(65) Prior Publication Data

US 2021/0386711 A1     Dec. 16, 2021

Related U.S. Application Data

(63) Continuation of application No. 17/154,676, filed on Jan. 21, 2021, now Pat. No. 11,103,482, which is a continuation of application No. 17/064,915, filed on Oct. 7, 2020, now Pat. No. 10,898,573, which is a continuation of application No. 16/715,998, filed on Dec. 16, 2019, now Pat. No. 10,814,001.

(60) Provisional application No. 62/844,069, filed on May 6, 2019, provisional application No. 62/843,819, filed on May 6, 2019.

(51) Int. Cl.

| A61K 31/4164 | (2006.01) |
|---|---|
| A61K 9/48 | (2006.01) |
| A61K 47/02 | (2006.01) |
| A61K 47/12 | (2006.01) |
| A61K 47/38 | (2006.01) |
| A61P 27/02 | (2006.01) |
| A61F 9/08 | (2006.01) |
| A61K 9/00 | (2006.01) |
| A61F 9/00 | (2006.01) |

(52) U.S. Cl.
CPC ........ *A61K 31/4164* (2013.01); *A61F 9/0008* (2013.01); *A61K 9/0048* (2013.01); *A61K 47/02* (2013.01); *A61K 47/12* (2013.01); *A61K 47/38* (2013.01); *A61P 27/02* (2018.01)

(58) Field of Classification Search
CPC .. A61K 31/4164; A61K 9/0048; A61K 47/02; A61K 47/12; A61K 47/38; A61P 27/02; A61F 9/0008
See application file for complete search history.

(56) References Cited

U.S. PATENT DOCUMENTS

| 4,425,345 A | 1/1984 | Horlington et al. |
|---|---|---|
| 5,459,133 A | 10/1995 | Neufield |
| 5,888,493 A | 3/1999 | Sawaya |
| 7,812,049 B2 | 10/2010 | Shanler et al. |
| 8,357,714 B2 * | 1/2013 | Silverberg ........... A61K 31/137 514/396 |
| 8,420,688 B2 | 4/2013 | Shanler et al. |
| 8,685,439 B2 | 4/2014 | Chapin et al. |
| 8,709,508 B2 | 4/2014 | Jones et al. |
| 8,758,816 B2 | 6/2014 | Fuge et al. |
| 8,815,929 B2 | 8/2014 | Shanler et al. |
| 8,883,838 B2 | 11/2014 | Shanler et al. |
| 9,011,941 B2 | 4/2015 | Jones et al. |
| 9,018,240 B2 | 4/2015 | Silverberg |
| 9,867,808 B2 | 1/2018 | Silverberg |
| 9,974,773 B2 | 5/2018 | Sarpotdar et al. |
| 2007/0264318 A1 | 11/2007 | Chapin et al. |
| 2010/0173019 A1 | 7/2010 | Paik et al. |
| 2010/0311688 A1 * | 12/2010 | Chapin .................. A61P 27/04 514/57 |
| 2012/0225918 A1 | 9/2012 | Silverberg |
| 2012/0225920 A1 | 9/2012 | Silverberg |
| 2012/0264681 A1 * | 10/2012 | Braiman-Wiksman ..................... A61K 38/08 514/5.9 |
| 2014/0161903 A1 | 2/2014 | Chapin et al. |
| 2015/0045403 A1 | 2/2015 | Shanler et al. |
| 2015/0313894 A1 | 11/2015 | Graeber et al. |
| 2016/0038465 A1 | 2/2016 | Silverberg |
| 2018/0050026 A1 | 2/2018 | Mahadevan et al. |
| 2018/0071390 A1 | 3/2018 | Patel et al. |
| 2018/0147214 A1 | 5/2018 | Ostrow et al. |
| 2018/0263962 A1 | 5/2018 | Sarpotdar et al. |
| 2018/0325806 A1 | 7/2018 | Litvack et al. |
| 2018/0360827 A1 | 8/2018 | Shanler et al. |
| 2018/0312335 A1 | 11/2018 | Jacobsson et al. |
| 2018/0338953 A1 | 11/2018 | Silverberg |

(Continued)

FOREIGN PATENT DOCUMENTS

| CN | 103501771 A | 1/2014 |
|---|---|---|
| CN | 105997856 A | 10/2016 |

(Continued)

OTHER PUBLICATIONS

Künzi R, "Keeping Preservative-Free Eyedrops Sterile With the Steridrop™ Tube". ONdrugDelivery Magazine, Issue 94 (Jan. 2019), pp. 48-50.*

Anderson, R.L. et al., "The Levator Aponeurosis," Arch Opthalmol, 95:1437-41, American Medical Association, United States (1977).

Bear, C. et al., "Muller's Superior Tarsal Muscle: Anatomy Physiology, and Clinical Significance," Annals of Plastic Surgery, 14(4):324-33, Wolters Kluwer, United States (1985).

Custer, P.L., (2008) "Blepharoptosis," Yanoff, M., Duker J.S., editors. Ophthalmology. 3rd ed. St. Louis, MO: Mosby Elsevier; p. 1397-1403.

(Continued)

Primary Examiner — Jared Barsky

(74) Attorney, Agent, or Firm — Sterne, Kessler, Goldstein & Fox P.L.L.C.

(57) ABSTRACT

The present disclosure is directed to compositions comprising oxymetazoline and methods of stabilizing oxymetazoline compositions for long term storage.

29 Claims, 8 Drawing Sheets

(56) References Cited

U.S. PATENT DOCUMENTS

| | | |
|---|---|---|
| 2019/0008857 A1 | 1/2019 | Shanler et al. |
| 2020/0009114 A1 | 1/2020 | Silverberg |

FOREIGN PATENT DOCUMENTS

| | | |
|---|---|---|
| WO | WO 2009/114521 A1 | 9/2009 |
| WO | WO 2010/141831 A1 | 12/2010 |

OTHER PUBLICATIONS

Duzman, E. et al., "Topically Applied Oxymetazoline," *Arch Opthalmol*, 101:1122-6, American Medical Association, United States (1983).

Finsterer, J., "Ptosis: causes, presentation, and management," *Aesthetic Plast. Surg,.* 27(3):193-204, Springer Publishing, Germany (2003).

Fox, S.L. et al., "Oxymetazoline in the treatment of Allergic and non-infections conjunctivitis," *J Int Med Res*, 7:528-30, Cambridge Medical Publications Limited, England (1979).

Fraunfelder, F.T., et al., "Possible adverse effects from topical ocular 10% phenylephrine," *Am. J. Ophthalmol*, 85(4):447-53, Elsevier, Netherlands (1978).

Garcia-Campana, A.M. et al., "Flow injection analysis of oxymetazoline hydrochloride with inhibited chemiluminescent detection," *Analytica Chemica Acta*, 516:245-49, Elsevier, Netherlands (2004).

Hayes, F.J. et al., "Rapid liquid chromatographic-mass spectrometric assay for oxymetazoline in whole rat blood," *Journal of Chromatography*, 692:73-81, Elsevier, Netherlands (1995).

Ho, S.F. et al. "Modified visual field test for ptosis surgery (Leicester Peripheral Field Test)," *Eye (Lond).*, 25(3):365-9, Nature Publishing Group, England (2011).

Jarvinen, T. et al., "Prodrugs for improved ocular drug delivery," *Advanced Drug Delivery Reviews*, 19:203-224, Elsevier, Netherlands (1996).

Kass, M.A., "Dipivefrin and epinephrine treatment of elevated intraocular pressure: a comparative study," *Arch. Ophthalmol*, 97(10): 1865-6 American Medical Association, United States (1979).

Kersten, R.C., "Acquired ptosis in the young and middle-aged adult population," *Ophthalmology*, 102:924-8, Elsevier, Netherlands (1995).

Matjucha, I.C., "The nonsurgical treatment of ptosis," In: Cohen A. J., Weinberg D.A., editors: *Evaluation and Management of Blepharoptosis*, pp. 155-161 Springer, United States (2011).

Putterman, A.M. et al., "Muller Muscle-Conjuctiva Resection," *Arch Opthalmol*, 93:619-23, American Medical Association, United States (1975).

Rai, U.D.J.P. et al., "The suprachoroidal pathway: a new drug delivery route to the back of the eye," *Drug Discovery Today*, 20(4):491-5, Elsevier, Netherlands (2014).

Reddy, A.K. et al., "Ptosis in young soft contact lens wearers" *Ophthalmology*, 114:2370, American Academy of Ophthalmology (2007).

Schoenwald, R.D., "Ocular Dmg Delivery," *Clin Pharmacokinet*, 18(4):255-269, ADIS Press Limited, United States (1990).

Sherma, S.E. et al., "Intrathecal oxymetazoline produces analgesia via spinal alpha-adrenoceptors and potentiates spinal morphine," *European Journal of Pharmacology*, 148:371-80, Elsevier, Netherlands (1988).

Svensson, C. et al., "Topical vasoconstrictor (oxymetazoline) does not affect histamine-induced mucosal exudation of plasma in human nasal airways," *Clinical and Experimental Allergy*, 22:411-6, Wiley-Liss, United States (1992).

Scheinfeld, N., "The Use of Apraclonidine Eyedrops to Treat Ptosis After the Administration of Botulinum Toxin to the Upper Face," *Dermatol. Online J.*, 11(1):9, University of California, Davis, United States (2005).

Shah-Desa,; S.D. et al. "Scleral Contact Lens Usage in Patients With Complex Blepharoptosis," *Ophthal. Plast. Reconstr. Surg.*, 27(2):95-8, Wolters Kluwer, United States (2011).

Sridhara,; G. V., et al. "A., Community Survey of Ptosis of the Eyelid and Pupil Size of Elderly People, " *Age and Ageing*, 24(1): 21-4 , Oxford Press, England (1995).

Urtti, A. et al., "Systemic Absorption of Ocular Pilocarpine is Modified by Polymer Matrices," *International Journal of Pharmaceutics*, 23:147-161, Elsevier, Netherlands (1985).

Van Den Bosch, WA, et al., "Blepharoptosis Induced by Prolonged Hard Contact Lens Wear," Ophthalmology 99:1759-65, *American Academy of Ophthalmology*, United States (1992).

Vajpayee, R.B. et al., "Management of benign red eye (evaluation of topical oxymetazoline—a double masked study," *Indian Journal of Ophthalmology*, 34(1)33-6, All India Ophthalmological Society, India (1986).

Xuan, B. et al., "Efficacy of Oxymetazoline eye drops in non-infections conjunctivitis, the most common cause of acute red eyes," *Journal of Ocular Pharmacology*, 13(4):363-7, Mary Ann Liebert Publishing, United States (1997).

Yamamoto, A. et al., "The Ocular Route for Systemic Insulin Delivery in the Albino Rabbit," *The Journal of Pharmacology and Experimental Therapeutics*, 249(1):249-55, The American Society for Pharmacology and Experimental Therapeutics, United States (1989).

Lalezary, M. et al., "Blepharoptosis Associated Superior Visual Field Loss Detected With an Automated Screening Test," *Investigative Ophthalmology & Visual Science*, 50: abstract 5048, ARVO Annual Meeting (Apr. 2009).

Rowe, et al., "Methylcellulose," Handbook of Pharmaceutical Excipients, Sixth Edition, pp. 438-442, Pharmaceutical Press and the American Pharmacists Association, United States (2009).

Urs, L., "Blow-Fill-Seal for Ophthalmic Packaging," Innovations in Pharmaceutical Technology, available at www.iptonline.com/articles/public/page122nonprint.pdf, Google date sheet, 3 pages (Apr. 19, 2007).

U.S. Pharmacopeia, Oxymetazoline Hydrochloride Ophthalmic Solution, available at http://ftp.uspbpep.com/v29240/usp29nf24s0_m59635.html, Google entry date sheet included, 2 pages (Jan. 1, 2007).

International Search Report and Written Opinion dated Jul. 27, 2020, in International Application No. PCT/US2020/031425, EPO, Netherlands, 9 pages.

Amcor Rigid Plastics, "Child-proof closures for ophthalmic packaging," European Plastic Product Manufacturer published Oct. 27, 2015; accessed at https://www.eppm.com/materials/child-proof-closures-for-ophthalmic-packaging/.

* cited by examiner

STABILITY REPORT
Oxymetazoline Hydrochloride Ophthalmic Solution, 0.1%; LOT# R60681
Study Purpose: Research and Development
Condition: Real Time (25°C ± 2°C/ 60% ± 5% RH)
Orientation: Horizontal

| NO. | TEST | SPECIFICATION | TEST METHOD | TIME (MONTH) | 24 | 30 |
|---|---|---|---|---|---|---|
| | | | | PULL DATE | 12/05/18 | 06/28/19 |
| 1 | Description | Clear, colorless to slightly yellow solution free of any particulates or crystallization. | CTM-SC-AS-6714 | | Conforms | Conforms |
| | | | | TEST COMPLETION DATE | 12/12/18 | 07/02/19 |
| 2 | Osmolality | 290 - 365 mOsm/kg | SOP-SC-AS-6428 | | 337 mOsm/kg | 325 mOsm/kg |
| | | | | TEST COMPLETION DATE | 12/10/18 | 07/07/19 |
| 3 | pH | 5.8 - 6.8 | SOP-SC-AS-6112 | | 6.4 | 6.4 |
| | | | | TEST COMPLETION DATE | 12/13/18 | 07/03/19 |
| 4 | Assay | 90.0% - 110.0% label claim | CTM-SC-AS-6540 | | 101.7% | 104.4% |
| | | | | TEST COMPLETION DATE | 01/03/19 | 07/12/19 |
| 5 | Related Substances | Specifications: | CTM-SC-AS-6548 | | [1] | [1] |
| | A. Related Compound A | A. NMT 2.5% | | | A. 1.0% | A. 0.5% |
| | B. Mono-Hydroxylated T-Butyl Group of Related Compound A Isomers | B. NMT 1.0% | | | B. 0.1% | B. ND |
| | C. Hydroxylated Imidazoline | C. NMT 1.0% | | | C. 0.3% | C. ND |
| | D. Hydroxylamine Derivative | D. NMT 1.0% | | | D. 0.5% | D. ND |
| | E. Oxymetazoline N-Oxide | E. NMT 1.0% | | | E. 0.1% | E. ND |
| | F. Each Individual Unknown Impurity | F. NMT 0.1% | | | F. <0.1% (RRT 0.293) | F. 0.1 % (RRT 0.305)<br><0.1% (RRT 1.187)<br><0.1% (RRT 1.236)<br><0.1% (RRT 1.288)<br><0.1% (RRT 1.414)<br>0.1% (RRT 1.610)<br>0.1% (RRT 1.827) |
| | G. Total Impurities | G. NMT 3.5% | | | G. 1.9% | G. 0.8% |
| | | | | TEST COMPLETION DATE | 01/03/19 | 07/19/19 |
| 6 | Viscosity | 15-35 cPs | CTM-SC-AS-6660 | | 26 cPs | 26 cPs |
| | | | | TEST COMPLETION DATE | 01/02/19 | 07/09/19 |

[1] Related Substances tested per CTM-SC-AS-6548.

FIG. 3A

STABILITY REPORT
Oxymetazoline Hydrochloride Ophthalmic Solution, 0.1%; LOT# R60681
Study Purpose: Research and Development
Condition: Real Time (25°C ± 2°C/ 60% ± 5% RH)
Orientation: Horizontal

| NO. | TIME (MONTH) | | | 24 | 30 |
|---|---|---|---|---|---|
| | PULL DATE | | | 12/05/18 | 06/28/19 |
| | TEST | SPECIFICATION | TEST METHOD | | |
| 7 | Weight Loss | NMT 5.0% | CTM-SC-AS-6509 | 0.4% | Not Tested |
| | TEST COMPLETION DATE | | | 12/6/18 | |
| 8 | Particulate Matter<br>A. ≥ 10 μm<br>B. ≥ 25 μm<br>C. ≥ 50 μm | Specifications:<br>A. NMT 50/mL<br>B. NMT 5/mL<br>C. NMT 2/mL | USP<789><br>microscopic method | | A. 1<br>B. 0<br>C. 0 |
| | TEST COMPLETION DATE | | | | 07/22/19 |
| 9 | Dye Ingress Immersion Test | No visual evidence of dye ingress and absorbance does not occur at approximately 665 nm. | MTM-SC-MB-6380 | | Conforms |
| | TEST COMPLETION DATE | | | | 07/11/19 |
| 10 | Sterility | No microbial growth is observed | MTM-SC-MB-6308 USP<71> | Conforms | Conforms |
| | TEST COMPLETION DATE | | | 01/01/19 | 07/19/19 |

FIG. 3B

STABILITY REPORT
Oxymetazoline Hydrochloride Ophthalmic Solution, 0.1%; LOT# R60701
Study Purpose: Research and Development
Condition: Real Time (25°C ± 2°C/ 60% ± 5% RH)
Orientation: Horizontal

| NO. | | TIME (MONTH) | | 24 | 30 |
|---|---|---|---|---|---|
| | | PULL DATE | | 12/05/18 | 06/28/19 |
| | | SPECIFICATION | TEST METHOD | | |
| 1 | Description | Clear, colorless to slightly yellow solution free of any particulates or crystallization. | CTM-SC-AS-6714 | Conforms | Conforms |
| | | | TEST COMPLETION DATE | 12/12/18 | 07/02/19 |
| 2 | Osmolality | 290 - 365 mOsm/kg | SOP-SC-AS-6428 | 322 mOsm/kg | 341 mOsm/kg |
| | | | TEST COMPLETION DATE | 12/10/18 | 07/07/19 |
| 3 | pH | 5.8-6.8 | SOP-SC-AS-6112 | 6.3 | 6.4 |
| | | | TEST COMPLETION DATE | 12/13/18 | 07/03/19 |
| 4 | Assay | 90.0% - 110.0% label claim | CTM-SC-AS-6540 | 102.9% | 99.8% |
| | | | TEST COMPLETION DATE | 01/03/19 | 07/12/19 |
| 5 | Related Substances | Specifications: | | [1] | [1] |
| | A. Related Compound A | A. NMT 2.5% | | A. 1.0% | A. 0.5% |
| | B. Mono-Hydroxylated T-Butyl Group of Related Compound A Isomers | B. NMT 1.0% | | B. 0.1% | B. ND |
| | C. Hydroxylated Imidazoline | C. NMT 1.0% | | C. 0.3% | C. ND |
| | D. Hydroxylamine Derivative | D. NMT 1.0% | CTM-SC-AS-6548 | D. 0.4% | D. ND |
| | E. Oxymetazoline N-Oxide | E. NMT 1.0% | | E. 0.1% | E. ND |
| | F. Each Individual Unknown Impurity | F. NMT 0.1% | | F. <0.1% (RRT 0.293) | F. <0.1% (RRT 1.186)<br><0.1% (RRT 1.236)<br><0.1% (RRT 1.287)<br><0.1% (RRT 1.413)<br>0.1% (RRT 1.609)<br>0.1% (RRT 1.823) |
| | G. Total Impurities | G. NMT 3.5% | | G. 1.9% | G. 0.7% |
| | | | TEST COMPLETION DATE | 01/03/19 | 07/19/19 |
| 6 | Viscosity | 15-35 cPs | CTM-SC-AS-6660 | 30 cPs | 26 cPs |
| | | | TEST COMPLETION DATE | 01/02/19 | 07/09/19 |

[1] Related substances tested per CTM-SC-AS-6548.

FIG. 4A

STABILITY REPORT
Oxymetazoline Hydrochloride Ophthalmic Solution, 0.1%; LOT# R60701
Study Purpose: Research and Development
Condition: Real Time (25°C ± 2°C/ 60% ± 5% RH)
Orientation: Horizontal

| NO. | TEST | SPECIFICATION | TEST METHOD | TIME (MONTH) | 24 | 30 |
|---|---|---|---|---|---|---|
| | | | | PULL DATE | 12/05/18 | 06/28/19 |
| 7 | Weight Loss | NMT 5.0 % | CTM-SC-AS-6509 | | 0.8% | Not Tested |
| | | | TEST COMPLETION DATE | | 12/06/18 | |
| 8 | Particulate Matter<br>A. ≥ 10 µm<br>B. ≥ 25 µm<br>C. ≥ 50 µm | Specifications:<br>A. NMT 50/mL<br>B. NMT 5/mL<br>C. NMT 2/mL | USP<789><br>microscopic method | | | A. 1<br>B. 1<br>C. 0 |
| | | | TEST COMPLETION DATE | | | 07/22/19 |
| 9 | Dye Ingress Immersion Test | No visual evidence of dye ingress and absorbance does not occur at approximately 665 nm. | MTM-SC-MB-6380 | | | Conforms |
| | | | TEST COMPLETION DATE | | | 07/11/19 |
| 10 | Sterility | No microbial growth is observed | MTM-SC-MB-6308<br>USP<71> | | Conforms | Conforms |
| | | | TEST COMPLETION DATE | | 03/21/19 | 07/15/19 |

FIG. 4B

STABILITY REPORT
Oxymetazoline Hydrochloride Ophthalmic Solution, 0.1%; LOT# R60711
Study Purpose: Research and Development
Condition: Real Time (25°C ± 2°C/ 60% ± 5% RH)
Orientation: Horizontal

| NO. | TEST | SPECIFICATION | TEST METHOD | TIME (MONTH) | 24 | 30 |
|---|---|---|---|---|---|---|
|   |   |   |   | PULL DATE | 12/05/18 | 06/28/19 |
| 1 | Description | Clear, colorless to slightly yellow solution free of any particulates or crystallization. | CTM-SC-AS-6714 |   | Conforms | Conforms |
|   |   |   | TEST COMPLETION DATE |   | 12/12/18 | 07/02/19 |
| 2 | Osmolality | 290 - 365 mOsm/kg | SOP-SC-AS-6428 |   | 302 mOsm/kg | 327 mOsm/kg |
|   |   |   | TEST COMPLETION DATE |   | 12/10/18 | 07/07/19 |
| 3 | pH | 5.8 - 6.8 | SOP-SC-AS-6112 |   | 6.3 | 6.4 |
|   |   |   | TEST COMPLETION DATE |   | 12/13/18 | 07/03/19 |
| 4 | Assay | 90.0% - 110.0% label claim | CTM-SC-AS-6540 |   | 92.8% | 105.2% |
|   |   |   | TEST COMPLETION DATE |   | 01/03/19 | 07/12/19 |
| 5 | Related Substances | Specifications: |   |   | [1] | [1] |
|   | A. Related Compound A | A. NMT 2.5% |   |   | A. 0.8% | A. 0.4% |
|   | B. Mono-Hydroxylated T-Butyl Group of Related Compound A Isomers | B. NMT 1.0% |   |   | B. 0.1% | B. ND |
|   | C. Hydroxylated Imidazoline | C. NMT 1.0% | CTM-SC-AS-6548 |   | C. 0.3% | C. ND |
|   | D. Hydroxylamine Derivative | D. NMT 1.0% |   |   | D. 0.4% | D. ND |
|   | E. Oxymetazoline N-Oxide | E. NMT 1.0% |   |   | E. 0.1% | E. ND |
|   | F. Each Individual Unknown Impurity | F. NMT 0.1% |   |   | F. <0.1% (RRT 0.292) | F. <0.1% (RRT 1.187)<br><0.1% (RRT 1.239)<br><0.1% (RRT 1.286)<br><0.1% (RRT 1.413)<br>0.1% (RRT 1.605)<br>0.1% (RRT 1.824) |
|   | G. Total Impurities | G. NMT 3.5% |   |   | G. 1.6% | G. 0.6% |
|   |   |   | TEST COMPLETION DATE |   | 01/03/19 | 07/19/19 |
| 6 | Viscosity | 15-35 cPs | CTM-SC-AS-6660 |   | 22 cPs | 24 cPs |
|   |   |   | TEST COMPLETION DATE |   | 01/02/19 | 07/09/19 |

[1] Related substances tested per CTM-SC-AS-6548.

FIG. 5A

STABILITY REPORT
Oxymetazoline Hydrochloride Ophthalmic Solution, 0.1%; LOT# R60711
Study Purpose: Research and Development
Condition: Real Time (25°C ± 2°C/ 60% ± 5% RH)
Orientation: Horizontal

| | TIME (MONTH) | | | 24 | 30 |
|---|---|---|---|---|---|
| | PULL DATE | | | 12/05/18 | 06/28/19 |
| NO. | TEST | SPECIFICATION | TEST METHOD | | |
| 7 | Weight Loss | NMT 5.0% | CTM-SC-AS-6509 | 0.2% | Not Tested |
| | | | TEST COMPLETION DATE | 12/06/18 | |
| 8 | Particulate Matter<br>A. ≥ 10 μm<br>B. ≥ 25 μm<br>C. ≥ 50 μm | Specifications:<br>A. NMT 50/mL<br>B. NMT 5/mL<br>C. NMT 2/mL | USP<789><br>microscopic method | | A. 3<br>B. 1<br>C. 0 |
| | | | TEST COMPLETION DATE | | 07/22/19 |
| 9 | Dye Ingress Immersion Test | No visual evidence of dye ingress and absorbance does not occur at approximately 665 nm. | MTM-SC-MB-6380 | | Conforms |
| | | | TEST COMPLETION DATE | | 07/11/19 |
| 10 | Sterility | No microbial growth is observed | MTM-SC-MB-6308<br>USP<71> | Conforms | Conforms |
| | | | TEST COMPLETION DATE | 01/01/19 | 07/15/19 |

FIG. 5B

OXYMETAZOLINE COMPOSITIONS

FIELD OF THE INVENTION

This invention relates to compositions comprising oxymetazoline, pharmaceutically acceptable salts of oxymetazoline, and methods for preparing and using them.

BACKGROUND OF THE INVENTION

Blepharoptosis (commonly known as ptosis) is abnormal partial or complete drooping of the upper eyelid that usually occurs from a partial or complete dysfunction of the muscles that elevate the upper eyelid: the levator palpebrae superioris and/or the Müller's muscle. Ptosis occurs when the muscles that raise the eyelid (levator palpebrae superioris and/or Müller's muscles) are not strong enough to do so properly. It can affect one eye or both eyes and is more common in the elderly, as muscles in the eyelids begin to deteriorate. It is one of the most common eyelid disorders, occurring in approximately 12% of adults over the age of 50 (G. V. Sridharan, R. C. Tallis, B. Leatherbarrow, W. M. Forman, A., Community Survey of Ptosis of the Eyelid and Pupil Size of Elderly People, *Age and Ageing*, Volume 24, Issue 1, January 1995, pp. 21-24). Ptosis is classified as either congenital or acquired. Acquired ptosis has numerous etiologies but most often is aponeurotic, a result of involutional changes to the levator aponeurosis or a result of stretching or disruption during cataract surgery, lens replacement, or as a result of long-term contact lens wear, both hard and soft lenses. (Custer P. L., (2008) Blepharoptosis. In: Yanoff M., Duker J. S., editors. Ophthalmology. 3rd ed. St. Louis, Mo.: Mosby Elsevier; p. 1397-1403; van den Bosch W A, Lemij H. G., Blepharoptosis induced by prolonged hard contact lens wear. Ophthalmology. 1992; 99:1759-65; Kersten R. C., Conciliis C., Kulwin D. R., Acquired ptosis in the young and middle-aged adult population. Ophthalmology. 1995; 102: 924-8; Reddy A. K., Foroozan R., Arat Y. O., Edmond J. C., Yen M. T., Ptosis in young soft contact lens wearers. Ophthalmology. 2007; 114:2370.)

Patients with ptosis may experience significant superior visual field defects, which can affect daily activities such as driving, crossing streets, and reading. Treatment for acquired ptosis usually involves surgery, with risks of infection, bleeding, over- or under-correction, reduced vision, and lagophthalmos (inability to close the eyelids completely) (Finsterer J., Ptosis: causes, presentation, and management. Aesthetic Plast. Surg. 2003; 27(3):193-204). Mechanical treatment of ptosis (scleral contact lenses with a bar to lift the eyelid, eyelid ptosis crutches attached to glasses, or adhesive tape or putty to affix the upper eyelid to the supraorbital structures) is limited by patient dissatisfaction with physical appearance, contact allergies, or skin irritation. (Shah-Desai S. D., Aslam S. A., Pullum K., Beaconsfield M., Rose G. E., Scleral contact lens usage in patients with complex blepharoptosis. Ophthal. Plast. Reconstr. Surg. 2011 March-April; 27(2):95-8.) Pharmacologic treatment of ptosis has not been pursued because the agents that have been evaluated (e.g., epinephrine, dipivefrin, apraclonidine, phenylephrine, brimonidine) either caused mydriasis, resulting in blurred vision or photophobia, or unacceptable systemic side effects. (Matjucha I. C., The nonsurgical treatment of ptosis. In: Cohen A. J., Weinberg D. A., editors: Evaluation and management of blepharoptosis. New York: Springer, 2011. pp. 155-61; Scheinfeld N., The use of apraclonidine eyedrops to treat ptosis after the administration of botulinum toxin to the upper face. Dermatol. Online J. 2005 Mar. 1; 11(1):9; Kass M. A., Mandell A. I., Goldberg I., Paine J. M., Becker B., Dipivefrin and epinephrine treatment of elevated intraocular pressure: a comparative study. Arch. Ophthalmol. 1979 October; 97(10):1865-6; Fraunfelder F. T., Scafidi A. F., Possible adverse effects from topical ocular 10% phenylephrine. Am. J. Ophthalmol. 1978; 85(4):447-53.)

Oxymetazoline hydrochloride, 6-tert-Butyl-3-(2-imidazolin-2-ylmethyl)-2,4-dimethylphenol monohydrochloride or Phenol, 3-[(4,5-dihydro-1H-imidazol-2-yl)methyl]-6-(1,1-dimethylethyl)-2,4-dimethyl-, monohydrochloride, is an α-adrenergic agonist. Oxymetazoline is a direct acting sympathomimetic amine, which acts on alpha-adrenergic receptors in the arterioles of the conjunctiva and nasal mucosa.

To address the ongoing challenge of balancing the efficacies with the relative risk of adverse events, a novel ophthalmic formulation of oxymetazoline hydrochloride was developed.

BRIEF SUMMARY OF THE INVENTION

In some aspects, the compositions of the present disclosure are related to an aqueous pharmaceutically stable ophthalmic formulation comprising: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally a pH adjuster; wherein the formulation has a pH range from about 6.3 to about 6.5. In some aspects, the one or more suitable buffers comprise from about 0.05 wt % to about 1.0 wt %. In some aspects, the one or more suitable buffers comprise sodium acetate trihydrate and sodium citrate. In some aspects, the one or more suitable buffers comprise about 0.39 wt % sodium acetate trihydrate and about 0.17 wt % sodium citrate. In some aspects, the formulation comprises about 0.64 wt % sodium chloride, about 0.075 wt % potassium chloride, about 0.048 wt % calcium chloride dihydrate, and about 0.03 wt % magnesium chloride hexahydrate. In some aspects, the pH adjuster is selected from the group consisting of acetic acid, hydrochloric acid, sulfuric acid, fumaric acid, phosphoric acid, calcium acetate, calcium carbonate, ammonium bicarbonate, ammonium sulfate, sodium hydroxide, ammonium hydroxide, ammonium phosphate, and a combination thereof. In some aspects, the pH adjuster comprises hydrochloric acid. In some aspects, the formulation does not comprise a preservative. In some aspects, the formulation is stable for a period of 0-24 months. In some aspects, the formulation is stable for a period of at least 24 months. In some aspects, the formulation is stable at 25° C. and 40% relative humidity for a period of at least 24 months. In some aspects, the composition is formulated in a single use container. In some aspects, the volume of the single use container is about 0.5 mL. In some aspects, the single use container is in child resistant packaging. In some aspects, the single use container delivers about 0.035 mg of oxymetazoline hydrochloride per drop.

The compositions of the present disclosure are also related to an aqueous pharmaceutically stable ophthalmic formulation consisting of: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally a pH adjuster; wherein the formulation has a pH range from about 6.3 to about 6.5. In some aspects, the one or more suitable buffers comprise from about 0.05 wt % to about 1.0 wt %. In some aspects, the one or more suitable buffers comprise sodium acetate trihydrate and sodium citrate. In some aspects, the one or more suitable buffers comprise about 0.39 wt % sodium acetate trihydrate and about 0.17 wt % sodium citrate. In some aspects, the formulation comprises about 0.64 wt % sodium chloride, about 0.075 wt % potassium chloride, about 0.048 wt % calcium chloride dihydrate, and about 0.03 wt % magnesium chloride hexahydrate. In some aspects, the pH adjuster is selected from the group consisting of acetic acid, hydrochloric acid, sulfuric acid, fumaric acid, phosphoric acid, calcium acetate, calcium carbonate, ammonium bicarbonate, ammonium sulfate, sodium hydroxide, ammonium hydroxide, ammonium phosphate, and a combination thereof. In some aspects, the pH adjuster comprises hydrochloric acid. In some aspects, the formulation is stable for a period of 0-24 months. In some aspects, the formulation is stable for a period of at least 24 months. In some aspects, the formulation is stable at 25° C. and 40% relative humidity for a period of at least 24 months. In some aspects, the composition is formulated in a single use container. In some aspects, the volume of the single use container is about 0.5 mL. In some aspects, the single use container is in child resistant packaging. In some aspects, the single use container is in a child resistant pouch. In some aspects, the single use container delivers about 0.035 mg of oxymetazoline hydrochloride per drop.

The compositions of the present disclosure are also related to an aqueous pharmaceutically stable ophthalmic preservative-free formulation comprising: about 0.1 wt % oxymetazoline hydrochloride; about 0.64 wt % sodium chloride; about 0.075 wt % potassium chloride; about 0.048 wt % calcium chloride dihydrate; about 0.03 wt % magnesium chloride hexahydrate; one or more suitable buffers; about 0.5 wt % hypromellose; and optionally hydrochloric acid; wherein the formulation has a pH range from about 6.3 to about 6.5.

The methods of the present disclosure are related to a method of treating ptosis in a subject, comprising administering to at least one eye of the subject a therapeutically effective amount of an aqueous pharmaceutically stable ophthalmic preservative-free formulation comprising: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally hydrochloric acid; wherein the aqueous pharmaceutically stable ophthalmic formulation has a pH range from about 6.3 to about 6.5. In some aspects, the ptosis is acquired blepharoptosis. In some aspects, the formulation is administered to the subject on one or more consecutive days at a dose of one drop in each eye for a total daily dose of about 0.07 mg oxymetazoline hydrochloride.

In some aspects, a mean $C_{max}$ after a single-dose administration of the formulation is from about 25 to about 35 pg/ml. In some aspects, a mean $AUC_{0-\infty}$ after a single-dose administration of the formulation is from about 300 to about 700 pg·h/mL. In some aspects, a $T_{max}$ after a single-dose administration of the formulation is from about 0.5 to about 6 hours. In some aspects, the methods of the present disclosure are related to a method of treating ptosis using an aqueous pharmaceutically stable ophthalmic preservative-free formulation comprising: about 0.64 wt % sodium chloride; about 0.075 wt % potassium chloride; about 0.048 wt % calcium chloride dihydrate; about 0.03 wt % magnesium chloride hexahydrate; and about 0.5 wt % hypromellose.

The methods of the present disclosure are also related to a method of increasing the vertical separation of the upper and lower eyelids in a subject, comprising administering to at least one eye of the subject an aqueous pharmaceutically stable ophthalmic preservative-free formulation comprising: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally hydrochloric acid; wherein the aqueous pharmaceutically stable ophthalmic formulation has a pH range from about 6.3 to about 6.5.

In some aspects, the formulation is administered to the subject on one or more consecutive days at a dose of one drop in a single eye for a total daily dose of about 0.035 mg oxymetazoline hydrochloride. In some aspects, the formulation is administered to the subject on one or more consecutive days at a dose of one drop in each eye for a total daily dose of about 0.07 mg oxymetazoline hydrochloride. In some aspects, a mean $C_{max}$ after a single-dose administration of the formulation is from about 25 to about 35 pg/ml. In some aspects, a mean $AUC_{0-\infty}$ after a single-dose administration of the formulation is from about 300 to about 700 pg·h/mL. In some aspects, a $T_{max}$ after a single-dose administration of the formulation is from about 0.5 to about 6 hours.

In some aspects, the aqueous pharmaceutically stable ophthalmic preservative-free formulation comprises: about 0.64 wt % sodium chloride; about 0.075 wt % potassium chloride; about 0.048 wt % calcium chloride dihydrate; about 0.03 wt % magnesium chloride hexahydrate; and about 0.5 wt % hypromellose.

The methods of the present disclosure are also directed to a method of improving a Leicester Peripheral Field Test (LPFT) score in a subject, comprising administering to at least one eye of the subject an aqueous pharmaceutically stable ophthalmic preservative-free formulation comprising: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally hydrochloric acid; wherein the aqueous pharmaceutically stable ophthalmic formulation has a pH range from about 6.3 to about 6.5, and whereby the mean LPFT score is increased by about 5-10 points after about 0.1-16 hours after administration. In some aspects, the formulation is administered to the subject on one or more consecutive days at a dose of one drop in each eye for a total daily dose of about 0.07 mg oxymetazoline hydrochloride. In some aspects, a mean $C_{max}$ after a single-dose administration of the formulation is from about 25 to about 35 pg/ml. In some aspects, a mean $AUC_{0-\infty}$ after a single-dose administration of the formulation is from about 300 to about 700 pg·h/mL. In some aspects, a $T_{max}$ after a single-dose administration of the formulation is from about 0.5 to about 6 hours. In some aspects, the Leicester Peripheral Field Test (LPFT) median score is increased by about 5-10 points after about 6 hours after administration. In some aspects, tachyphylaxis is not exhibited for at least six weeks. In some aspects, the aqueous pharmaceutically stable ophthalmic preservative-free formulation comprises: about 0.64 wt % sodium chloride; about 0.075 wt % potassium chloride; about 0.048 wt % calcium chloride dihydrate; about 0.03 wt % magnesium chloride hexahydrate; and about 0.5 wt % hypromellose.

The methods of the present disclosure are also related to a method of improving a Marginal Reflex Distance Test 1 (MRD-1) score in a subject, comprising administering to at least one eye of the subject an aqueous pharmaceutically stable ophthalmic preservative-free formulation comprising: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally hydrochloric acid; wherein the aqueous pharmaceutically stable ophthalmic formulation has a pH range from about 6.3 to about 6.5, and whereby the mean score is increased by about 0.2-1.5 points after about 1-20 minutes after administration or after about 1-6 hours, e.g., 8 hours, after administration. In some aspects, the aqueous pharmaceutically stable ophthalmic formulation is administered to the subject on one or more consecutive days at a dose of one drop in each eye for a total daily dose of about 0.07 mg oxymetazoline hydrochloride. In some aspects, a mean $C_{max}$ after a single-dose administration of the formulation is from about 25 to about 35 pg/ml. In some aspects, a mean $AUC_{0-\infty}$ after a single-dose administration of the formulation is from about 300 to about 700 pg·h/mL. In some aspects, a $T_{max}$ after a single-dose administration of the formulation is from about 0.5 to about 6 hours. In some aspects, the Marginal Reflex Distance Test 1 (MRD-1) mean score is increased by about 0.2-1.0 points after about 5 minutes after administration. In some aspects, tachyphylaxis is not exhibited for at least six weeks. In some aspects, the aqueous pharmaceutically stable ophthalmic preservative-free formulation comprises: about 0.64 wt % sodium chloride; about 0.075 wt % potassium chloride; about 0.048 wt % calcium chloride dihydrate; about 0.03 wt % magnesium chloride hexahydrate; and about 0.5 wt % hypromellose. In some aspects, the use of the present compositions and methods does not exhibit tachyphylaxis. In some aspects, tachyphylaxis is not exhibited for 6 weeks. In some aspects, tachyphylaxis is not exhibited for a period of 6 weeks to 3 months. In some aspects, tachyphylaxis is not exhibited for a period of 6 weeks, 7 weeks, 8 weeks, 9 weeks, 10 weeks, 11 weeks, 1 month, 2 months, or 3 months. In some aspects, tachyphylaxis is not exhibited during use of the compositions or methods of the present invention.

BRIEF DESCRIPTION OF THE DRAWINGS

FIGS. 3A and 3B show 24-month and 30-month stability data for oxymetazoline composition batch R60681.

FIGS. 4A and 4B show 24-month and 30-month stability data for oxymetazoline composition batch R60701.

FIGS. 5A and 5B show 24-month and 30-month stability data for oxymetazoline composition batch R60711.

DETAILED DESCRIPTION OF THE INVENTION

I. Definitions

Figure 1:
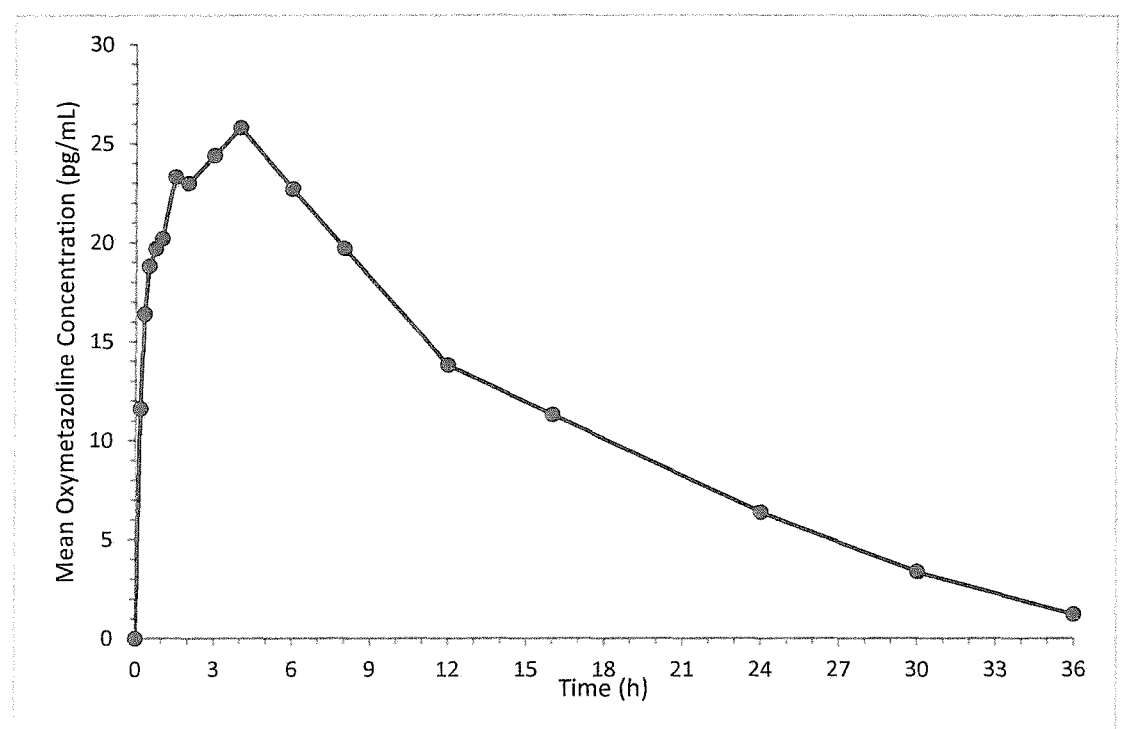
FIG. 1 shows the mean concentration reached after single-dose topical administration of 0.1 wt % oxymetazoline HCl ophthalmic solution using one drop in each eye.

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

In order to further define this disclosure, the following terms and definitions are provided.

The singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "about" is used herein to mean about, roughly, around, or in the regions of When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically stable" means the ability of the pharmaceutical dosage form to maintain the physical, chemical, therapeutic and microbial properties during the time of storage and usage by the patient.

The term "effective amount" or "pharmaceutically effective amount" as used herein refers to the amount or quantity of a drug or pharmaceutically active substance which is sufficient to elicit the required or desired therapeutic response, or in other words, the amount which is sufficient to elicit an appreciable biological response when administered to a patient.

The term "unit dosage form" or "unit dose composition" as used herein refers to a device containing a quantity of the therapeutic compound, said quantity being such that one or more predetermined units may be provided as a single therapeutic administration.

The term "wt %" or "weight/volume" as used herein refers to the ratio between to components with respect to volume. For example, a 5 wt % ethanol in water solution would represent a solution comprising 5 g ethanol for every 100 mL water.

The term "$C_{max}$" as used herein refers to the maximum plasma concentration of a drug after it is administered to a subject.

The term "$T_{max}$" as used herein refers to the time required to reach the maximal plasma concentration ("$C_{max}$") after administration of a drug.

The term "AUC" as used herein refers to the area under the curve of a plot of plasma concentration versus time following administration of a drug.

The term "$AUC_{0-t}$" as used herein refers to the area under the drug concentration-time curve from time zero to the time of the last measurable concentration ($C_t$).

The term "$AUC_{0-\infty}$" as used herein refers to the area under the drug concentration-time curve from time zero to infinity. $AUC_{0-\infty}$ is calculated to the last measured concentration ($AUC_{0-T}$) and extrapolated to infinity ($AUC_{t-\infty}$), for extent of absorption of a drug.

As used herein, the term "free base equivalent" or "FBE" refers to the amount of oxymetazoline present in the oxymetazoline or salt thereof. In other words, the term "FBE" means either an amount of oxymetazoline free base, or the equivalent amount of oxymetazoline free base that is provided by a salt of oxymetazoline. For example, due to the weight of the hydrochloride salt, 100 mg of oxymetazoline hydrochloride only provides as much oxymetazoline as 88 mg of the free base form of oxymetazoline. Other salts are expected to have different conversion factors, depending on the molecular weight of the salt.

The term "Leicester Peripheral Field Test" or "LPFT" refers to a customized visual field test designed specifically to assess ptosis (Ho S. F., Morawski A., Sampath R., Burns J., Modified visual field test for ptosis surgery (Leicester Peripheral Field Test). Eye (Lond). 2011 March; 25(3):365-9. doi:10.1038/eye.2010.210. Epub 2011 Jan. 21), and is performed using a Humphrey Visual Field Analyzer. It is an age-corrected screening test in which thirty-five points are tested in the superior field while 14 points are tested in the inferior field. A maximum of 48° is tested in the superior visual field. The center of fixation is shifted 15° inferiorly to allow for maximum superior field testing. The inferior field test serves as a reference but is not used in the analysis.

The term "Marginal Reflex Distance 1 (MRD)" refers to one of two tests. MRD-1 refers to a test that uses photographic measurement of the distance from the central pupillary light reflex to the central margin of the upper lid. External digital photographs are used to measure MRD-1. Measurements are taken based on the distance from the central pupillary light reflex to the central margin of the upper lid, ≤2 mm (no visible central pupillary light reflex defaults to 0). MRD-2 refers to the measurement of the vertical distance from the pupillary center and the lower eyelid margin.

The term "treating" or "treatment" as used herein refers to the administration of a composition to a subject for therapeutic purposes.

The term "mean" refers to an average value in a patient population. For example, a "mean $C_{max}$" refers to an average of the maximum plasma concentration values of a drug in a patient population.

The term "adult" refers to a person 18 years of age or older.

II. Composition

Compositions of the invention include an effective amount of an alpha-adrenergic agonist formulated for ophthalmic administration. The invention provides compositions and methods useful in the treatment of ptosis. In some aspects, the composition is an ophthalmic solution. In some aspects, oxymetazoline hydrochloride is formulated for topical ocular delivery as an aseptically prepared, sterile, preservative-free ophthalmic solution (eye drops). The ophthalmic solution can contain 0.1 wt % of oxymetazoline hydrochloride in a balanced salt solution with an added viscosity modifier (hypromellose). It can be filled into clear, unit-dose, 0.5-mL low-density polyethylene (LDPE) blow-fill-seal (BFS) vials, which can be individually packaged in foil pouches.

When administered at 0.1 wt %, oxymetazoline is believed to stimulate the a2 adrenergic receptors in Müller's muscle causing it to contract, thereby lifting the upper eyelid, and retracting the lower eyelid to a lesser degree.

In some aspects, the solution is an aqueous pharmaceutically stable ophthalmic formulation consisting of: about 0.1 wt % oxymetazoline hydrochloride; from about 0.2 wt % to about 1.0 wt % sodium chloride; from about 0.05 wt % to about 0.10 wt % potassium chloride; from about 0.02 wt % to about 0.06 wt % calcium chloride; from about 0.01 wt % to about 0.05 wt % magnesium chloride; one or more suitable buffers; from about 0.1 wt % to about 0.90 wt % hypromellose; and optionally a pH adjuster; wherein the formulation has a pH range from about 6.3 to about 6.5.

In some aspects, the one or more suitable buffers comprise from about 0.05 wt % to about 1.0 wt %. In some aspects, the one or more suitable buffers comprise sodium acetate trihydrate and sodium citrate. In some aspects, the formulation comprises about 0.64 wt % sodium chloride, about 0.075 wt % potassium chloride, about 0.048 wt % calcium chloride dihydrate, and about 0.03 wt % magnesium chloride hexahydrate. In some aspects, the pH adjuster is selected from the group consisting of acetic acid, hydrochloric acid, sulfuric acid, fumaric acid, phosphoric acid, calcium acetate, calcium carbonate, ammonium bicarbonate, ammonium sulfate, sodium hydroxide, ammonium hydroxide, ammonium phosphate, and a combination thereof. In some aspects, the pH adjuster comprises hydrochloric acid.

In some aspects, the solution is an aqueous pharmaceutically stable ophthalmic formulation comprising: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, tris(hydroxymethyl)aminomethane (TRIS), and various mixed phosphate buffers (including combinations of $Na_2HPO_4$, $NaH_2PO_4$, and $KH_2PO_4$) and mixtures thereof. In one aspect, the one or more suitable buffers comprise 0.39 wt % sodium acetate trihydrate and 0.17 wt % sodium citrate.

In some aspects, the solution is an aqueous pharmaceutically stable ophthalmic formulation consisting essentially of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In one aspects, the one or more suitable buffers comprise 0.39 wt % sodium acetate trihydrate and 0.17 wt % sodium citrate.

In some aspects, the solution is an aqueous pharmaceutically stable ophthalmic formulation consisting of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In one aspect, the one or more suitable buffers comprise 0.39 wt % sodium acetate trihydrate and 0.17 wt % sodium citrate.

One aspect of the invention is a method for treating ptosis in a subject. The method includes the step of administering an effective amount of oxymetazoline to an eye of a subject in need of such treatment. In some aspects, the method comprises administering to at least one eye of the subject a therapeutically effective amount of an aqueous pharmaceutically stable ophthalmic formulation comprising: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In one aspect, the one or more suitable buffers comprise 0.39 wt % sodium acetate trihydrate and 0.17 wt % sodium citrate.

In some aspects of the invention, the subject is a mammal. In another aspect, the mammal is a human.

In some aspects, the formulation is administered at a total daily dose of about 0.07 mg oxymetazoline hydrochloride. In some aspects, the average weight of one drop is 0.035 g. In some aspects, one drop is administered to each eye, and each drop contains approximately 0.035 mg of oxymetazoline hydrochloride (0.0308 mg oxymetazoline free base).

In some aspects, the method comprises administering to at least one eye a therapeutically effective amount of an aqueous pharmaceutically stable ophthalmic formulation consisting essentially of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In some aspects, the one or more suitable buffers comprise 0.39 wt % sodium acetate trihydrate and 0.17 wt % sodium citrate. In some aspects, the formulation is administered in an amount of about 0.07 mg.

In some aspects, the method comprises administering to at least one eye a therapeutically effective amount of an aqueous pharmaceutically stable ophthalmic formulation consisting of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In some aspects, the one or more suitable buffers comprise sodium acetate trihydrate, sodium citrate, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In some aspects, the one or more suitable buffers comprise 0.39 wt % sodium acetate trihydrate and 0.17 wt % sodium citrate.

In some aspects, the solution is an aqueous pharmaceutically stable ophthalmic formulation comprising: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In other aspects, the one or more suitable buffers comprise boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In some aspects, the one or more suitable buffers comprise 0.39 wt % sodium acetate trihydrate and 0.17 wt % sodium citrate.

In some aspects, the solution is an aqueous pharmaceutically stable ophthalmic formulation comprising about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1.0 wt % oxymetazoline hydrochloride. In some aspects, the solution is an aqueous pharmaceutically stable ophthalmic formulation comprising about 0.10 wt %, about 0.12 wt %, about 0.13 wt %, about 0.14 wt %, about 0.15 wt %, about 0.16 wt %, about 0.17 wt %, about 0.18 wt %, about 0.19 wt %, or about 0.20 wt % oxymetazoline hydrochloride. In some aspects, the solution is an aqueous pharmaceutically stable ophthalmic formulation comprising about 0.01 wt %, about 0.02 wt %, about 0.03 wt %, about 0.04 wt %, about 0.05 wt %, about 0.06 wt %, about 0.07 wt %, about 0.08 wt %, or about 0.09 wt % oxymetazoline hydrochloride.

In some aspects, the solution is an aqueous pharmaceutically stable ophthalmic formulation consisting essentially of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In other aspects, the one or more suitable buffers comprise boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In some aspects, the one or more suitable buffers comprise 0.39 wt % sodium acetate trihydrate and 0.17 wt % sodium citrate.

In some aspects, the solution is an aqueous pharmaceutically stable ophthalmic formulation consisting of: 0.1 wt % oxymetazoline hydrochloride; 0.64 wt % sodium chloride; 0.075 wt % potassium chloride; 0.048 wt % calcium chloride dihydrate; 0.03 wt % magnesium chloride hexahydrate; one or more suitable buffers; 0.5 wt % hypromellose; and optionally hydrochloric acid; wherein the formulation has a pH range from 6.3 to 6.5. In other aspects, the one or more suitable buffers comprise boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. In some aspects, the one or more suitable buffers comprise 0.39 wt % sodium acetate trihydrate and 0.17 wt % sodium citrate.

In one aspect, the formulation comprises sodium chloride, and the amount of sodium chloride in the formulation is about 0.2 wt %, about 0.3 wt %, about 0.4 wt %, about 0.5 wt %, about 0.6 wt %, about 0.7 wt %, about 0.8 wt %, about 0.9 wt %, or about 1.0 wt %.

In one aspect, the formulation comprises potassium chloride, and the amount of potassium chloride in the formulation is about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, or about 0.5 wt %.

In one aspect, the formulation comprises calcium chloride, and the amount of calcium chloride in the formulation is about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, or about 0.2 wt %.

In one aspect, the formulation comprises magnesium chloride, and the amount of magnesium chloride in the formulation is about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, or about 0.2 wt %.

In one aspect, the formulation comprises hypromellose, and the amount of hypromellose in the formulation is about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, or about 2.0 wt %.

In some aspects, the oxymetazoline is provided as a pharmaceutically acceptable salt of oxymetazoline. The term "pharmaceutically acceptable salt" is art-recognized, and refers to relatively non-toxic, inorganic and organic acid addition salts of compositions of the present invention or any components thereof, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include but are not limited to the hydroxides, carbonates, and bicarbonates of mania, sodium, lithium, potassium, calcium, magnesium, aluminum, zinc and the like. Salts can also be formed with suitable organic bases, including those that are non-toxic and strong enough to form such salts.

III. Composition Stability

The compositions of the present disclosure are stable. The long-term stability is an important attribute to consider when preparing ophthalmologic formulations, especially those formulations that do not contain a preservative. Various critical quality attributes must be maintained over the shelf life of a composition in order to ensure the long-term stability of the composition, including assay, osmolality, impurities, viscosity, weight loss, and sterility. These attributes are affected by various factors including temperature, relative humidity, and/or pH.

Osmolality is the concentration of all solutes in a given weight of water and is expressed as units of either osmolality and is an attribute important for the maintenance of an ophthalmologic formulation. Most subject's eyes have an osmolality of approximately 300 mOsm, and therefore it is important that any formulation administered to the eye is maintained near this range, e.g., about 290 to about 365 mOsm/kg, so that the formulation is well tolerated.

The stability of the pH of the solution is also important for comfort and safety. If elements of the ophthalmologic formulation change the pH over time, the formulation may become unstable. Also, a change in pH can lead to administration of a formulation that could damage the eye. Therefore, it is important that a desired physiological pH is maintained across the entire life of the formulation. Maintaining pH close to neutral and the natural pH of the eye is important for safety.

Viscosity is a quality of an ophthalmologic formulation that is critical to maintain residence time of the formulation in the eye. It is important that the viscosity of the formulation is maintained over the life of the formulation so that the viscosity is consistent and the delivery and residence time of the active ingredient is maintained. For example, in one aspect the viscosity is from about 15 to about 35 cPs to maintain residence time in the eye and eye comfort.

Unstable solutions can degrade over time to produce unwanted degradation products. These products can be the result of unwanted chemical reactions involving the active ingredient, including hydrolysis and oxidation. The instability of the solution with respect to degradation products can lead to both toxicity as a result of the production of these impurities, and a lower concentration of the active ingredient due to degradation. Unwanted degradation products include N-(2-Aminoethyl)-2-[4-(1,1-dimethylethyl)-3-hydroxy-2,6-dimethylphenyl]acetamide, hydroxylated imidazoline derivatives, hydroxylamine, and N-oxide derivatives. Non-limiting examples of degradation products produced from oxymetazoline degradation include:

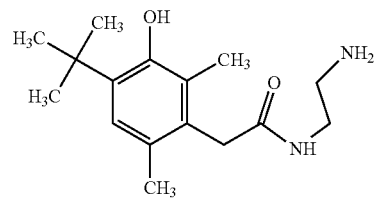

-continued

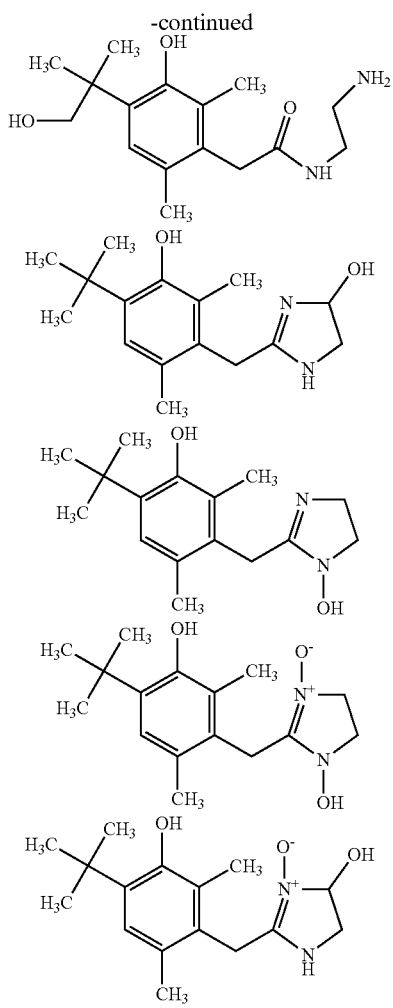

The presence of these degradation products must therefore be limited and monitored as a formulation ages, to prevent the potential loss of activity of the active ingredient and to prevent potential unwanted toxicity derived from any degradation products that develop.

Maintenance of the sterility of the formulation is also important. Sterility testing ensures that the ophthalmologic formulation is free from contamination of microorganisms, which could potentially lead to infection or other complications.

Maintenance of the water content in the formulation is important to maintain the desired concentration of components present in the formulation, and therefore a loss of water weight will affect the concentration of the components. Similarly, maintenance and monitoring of the degradation of components is also important because degradation products can also affect the concentration of the components, the pH of the solution, and can introduce unwanted contaminants that may pose a risk to the safety of the eye. The limit of degradation products is critical to drug product safety, and formulation and process variables can impact degradation products.

In some aspects, the compositions of the present disclosure are stable for about 3 months, about 6 months, about 9 months, about 12 months, about 14 months, about 18 months, about 21 months, about 24 months, about 30 months, about 36 months, about 42 months, about 48 months, about 54 months, or about 60 months. In some aspects, the compositions of the present disclosure are stable for about 3 months. In some aspects, the compositions of the present disclosure are stable for about 6 months. In some aspects, the compositions of the present disclosure are stable for at least about 9 months. In some aspects, the compositions of the present disclosure are stable for at least about 12 months. In some aspects, the compositions of the present disclosure are stable for about 14 months. In some aspects, the compositions of the present disclosure are stable for at least about 18 months. In some aspects, the compositions of the present disclosure are stable for about 21 months. In some aspects, the compositions of the present disclosure are stable for at least about 24 months. In some aspects, the compositions of the present disclosure are stable for at least about 30 months. In some aspects, the compositions of the present disclosure are stable for at least about 36 months. In some aspects, the compositions of the present disclosure are stable for at least about 42 months. In some aspects, the compositions of the present disclosure are stable for at least about 48 months. In some aspects, the compositions of the present disclosure are stable for at least about 54 months. In some aspects, the compositions of the present disclosure are stable for at least about 60 months.

Stability is also affected by the environmental conditions present during storage. For example, ambient temperature and/or humidity can affect long term stability of an ophthalmologic preparation. In some aspects, the compositions of the present disclosure are stable at temperature of from about 4° C. to about 30° C., about 4° C. to about 25° C., about 4° C. to about 20° C., about 10° C. to about 20° C., about 15° C. to about 20° C., or about 20° C. to about 30° C. In some aspects, the compositions of the present disclosure are stable at about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., or about 30° C.

In some aspects, the compositions of the present disclosure are stable at a relative humidity of from about 10% to about 70%, from about 20% to about 60%, from about 30% to about 50%, from about 20% to about 80%, from about 30% to about 70%, from about 40% to about 60%. In some aspects, the compositions of the present disclosure are stable at a relative humidity of from about 10% to about 70%. In some aspects, the compositions of the present disclosure are stable at a relative humidity of from about 40% to about 60%. In some aspects, the compositions of the present disclosure are stable at a relative humidity of about 10%, about 20%, about 30%, about 40%, about 50%, about 60%, about 70%, or about 80%. In some aspects, the compositions of the present disclosure are stable at a relative humidity of about 10%. In some aspects, the compositions of the present disclosure are stable at a relative humidity of about 20%. In some aspects, the compositions of the present disclosure are stable at a relative humidity of about 30%. In some aspects, the compositions of the present disclosure are stable at a relative humidity of about 40%. In some aspects, the compositions of the present disclosure are stable at a relative humidity of about 50%. In some aspects, the compositions of the present disclosure are stable at a relative humidity of about 60%. In some aspects, the compositions of the present disclosure are stable at a relative humidity of about 70%. In some aspects, the compositions of the present disclosure are stable at a relative humidity of about 80%.

IV. Methods of Treatment

The upper eyelids are normally lifted by contraction of the levator palpebrae superioris (levator) and Muller's (Mueller's) muscles. Ptosis creates a tired-looking appearance that can be cosmetically undesired; in more severe instances ptosis can interfere with vision in the affected eye(s). In addition to fatigue and age-related weakening of the levator and Muller's muscles as underlying causes of ptosis, there are a number of other conditions recognized to cause ptosis. For example, ptosis may also be due to a myogenic, neurogenic, aponeurotic, mechanical, or traumatic cause; it usually occurs isolated, but it may be associated with various other conditions, like hereditary, immunological, or degenerative disorders, tumors, and infections. The methods of the present disclosure are useful for the treatment of ptosis. In some aspects, a therapeutically effective amount of oxymetazoline hydrochloride is delivered in an ophthalmically acceptable carrier. In some aspects, the carrier is an emulsion, suspension, gel, ointment, or solution.

In a particular aspect, the solution is a topical ophthalmic solution administered as eye drops. Myogenic causes of ptosis can include diseases which may cause weakness in muscles or nerve damage, such as myasthenia gravis and chronic progressive external ophthalmoplegia. Dystrophy or dysgenesis of the elevator and/or Muller's muscles are the most common causes of congenital ptosis. Ptosis may be caused by damage to the third cranial nerve (oculomotor nerve) which controls the muscles which raise the upper eyelid. Congenital neurogenic ptosis is believed to be caused by Homer syndrome (also known as Homer's syndrome), in which a mild ptosis due to the paresis of the Muller muscle may be associated with ipsilateral miosis (pupillary constriction) and anhidrosis. Acquired Homer syndrome may result after trauma, neoplastic insult, or even vascular disease. Acquired ptosis is commonly caused by aponeurotic ptosis. This can occur as a result of senescence, dehiscence or disinsertion of the levator aponeurosis.

Moreover, chronic inflammation or intraocular surgery can lead to the same effect. Ptosis due to trauma can ensue after an eyelid laceration with transection of the upper eyelid elevator muscles or disruption of the neural input. Other causes of ptosis include eyelid neoplasms, neurofibromas, or the cicatrization after inflammation or surgery. Mild ptosis may occur with aging. It has been surprisingly found, through a process of evaluating a number of agents over a range of concentrations of such agents, that certain alpha adrenergic agonists, including in particular oxymetazoline HCl 0.1 wt %, provides a highly effective composition that produces surprising treatment outcomes as measured by Leicester Peripheral Field Test (LPFT) performance. It has been found that this composition can be used for the treatment of ptosis, lasting for 4-10 hours, or 6 hours in one aspect, following topical administration of a single drop of such agent to an affected eye.

It has been also surprisingly found, through a process of evaluating a number of agents over a range of concentrations of such agents, that certain alpha adrenergic agonists, including in particular oxymetazoline hydrochloride 0.1 wt %, provides a highly effective composition that produces surprising treatment outcomes as measured by Marginal Reflex Distance Test (MRD-1) performance. It has been found that this composition can be used for the treatment of ptosis, lasting for 4-10 hours, or 6 hours, following topical administration of a single drop of such agent to an affected eye. Rapid onset of the effects of the oxymetazoline hydrochloride 0.1 wt % was also found, with demonstrated improvement of ptosis 5 minutes after administration of the compositions of the present invention. It was also found that the MRD-1 performance improvement lasted for at least 6 hours after dose administration. It was also found that the MRD-1 performance improvement lasted for at least 8 hours. The compounds and methods of the present invention did not exhibit tachyphylaxis, which is a rapidly diminishing response to successive doses of a drug, rendering it less effective. In some aspects, tachyphylaxis is not exhibited for six weeks. In some aspects, tachyphylaxis is not exhibited for a period of six weeks to three months. In some aspects, tachyphylaxis is not exhibited for a period of 6 weeks, 7 weeks, 9 weeks, 10 weeks, 11 weeks, 1 months, 2 months, or 3 months. In some aspects, tachyphylaxis is not exhibited during use of the compositions or methods of the present invention. In some aspects, tachyphylaxis is not exhibited for a period of about 1 week, about 90 days, about 180 days, or about one year. In some aspects tachyphylaxis is not exhibited for a period of about 1 year, about 2 years, about 3 years, about 5 years, or about 10 years.

An aspect of the invention is a method for treating ptosis in a subject. The method includes the step of topically administering an effective amount of oxymetazoline to the exterior surface of an eye of a subject in need of such treatment. As used herein, "treating" means reducing, even if only temporarily, the severity of a condition or disease in a subject having such condition or disease. In one aspect the reducing is eliminating, even if only temporarily. For example, ptosis in a subject is said to be treated in accordance with the method if the ptosis is reduced or eliminated, even if only temporarily.

The methods of the present disclosure are also related to treating other eyelid diseases or unspecific conditions whereby the condition is treated by raising the eyelid. Other conditions that may be treated by the formulations of the present disclosure include Horner syndrome and Myasthenia gravis. The methods of the present disclosure can be used to treat other clinical conditions associated with eye, such as an eye disorder or an eye disease. The method includes administering to at least one eye of a subject in need of such a treatment a therapeutically effective amount of a composition of the present disclosure. In some aspects, the clinical condition associated with eye includes dry eye syndrome (e.g., keratoconjunctivitis sicca), Sjogren's syndrome, congenital alacrima, xerophthalmia (dry eye from vitamin A deficiency), keratomalacia, thyroid eye disease, ocular rosacea, eyelid disorders, meibomian gland disease, meibomian gland dysfunction, ectropion, blepharitis, blepharochalasis, sarcoidosis, stye, hordeolum, chalazion, ptosis, pterygium, eyelid edema, eyelid dermatitis, trichiasis, madarosis, dacryoadenitis, stevens-johnson syndrome, ocular graft versus host disease, dacryocystitis, conjunctivitis, keratoconjunctitis, blepharoconjunctivitis, blepharokeratoconjunctivitis, allergic conjunctivitis, vernal conjunctivitis, conjunctival suffusion, conjunctivochalasis, subconjunctival hemorrhage, pterygium, pinguecula, chemosis, iritis, iridocyclitis, glaucoma, ocular hypertension, red eye, keratitis, scleritis, episcleritis, peripheral ulcerative keratitis, neurotrophic keratitis, neurotrophic eye disease, corneal ulcer, ulcerative keratitis, corneal abrasion, photokeratitis, ultraviolet keratitis, exposure keratitis, and corneal dystrophy.

Other conditions include post-operative inflammation following ocular surgery (e.g. eyelid surgery, cataract surgery, corneal surgery, refractive surgery including photorefractive keratectomy, glaucoma surgery, lacrimal gland surgery, conjunctival surgery, eye muscle surgery, physical trauma, ocular conditions caused by the following autoimmune or vascular disorders: rheumatoid arthritis, juvenile rheumatoid arthritis, ankulosing spondylitis, reiter's syndrome, enteropathic arthritis, psoriatic arthritis, discoid and systemic lupus erythematosus, multiple sclerosis, graves' disease, antiphospholipid syndrome, sarcoidosis, wegner's granulomatosis, behcet's syndrome, polyarteritis nodosa, takayasu's arteritis, dermatomyositis, psoriasis, relapsing polychondritis, vasculitis, sickle cell-anemia, type II diabetes, diabetic retinopathy, and a combination thereof.

V. Dosing Frequency and Dose Escalation

According to the present invention, a subject (e.g., human) having or at risk of having ptosis is administered any of the pharmaceutical compositions described herein. In some aspects, the pharmaceutical compositions are administered at a constant, therapeutically-effective dose from the onset of therapy. The therapeutically-effective dose can contain 0.1 wt % oxymetazoline HCl and be one drop per eye. In one aspect, the dose comprises two drops of about 0.035 g/drop of a 0.1 wt % solution for a total dose of about 0.07 mg and wherein the pharmaceutical composition comprises about 0.035 mg oxymetazoline hydrochloride in each drop.

A pharmaceutical composition can be administered three times per day, twice per day, or once per day in a unit dose, wherein the total daily composition dose is about 0.005 g, about 0.01 g, about 0.02 g, about 0.03 g, about 0.04 g, about 0.05 g, about 0.06 g, about 0.07 g, about 0.08 g, about 0.09 g, or about 0.10 g. A pharmaceutical composition containing oxymetazoline hydrochloride 0.1 wt % can be administered three times per day, twice per day, or once per day in a unit dose, wherein the total daily oxymetazoline hydrochloride dose is about 0.050 mg, about 0.010 mg, about 0.020 mg, about 0.030 mg, about 0.035 mg, about 0.040 mg, about 0.050 mg, about 0.060 mg, about 0.070 mg, about 0.080 mg, about 0.090 mg, about 0.1 mg about 0.14 mg or about 0.21 mg. In some aspects, the pharmaceutical composition is administered three times per day, twice per day, or once per day in a unit dose in each eye. In some aspects, the total daily composition dose is about 0.07 mg, about 0.14 mg, or about 0.21 mg.

In some aspects, the formulation is administered in an amount of about 0.07 mg. In some aspects, the formulation is administered on one or more consecutive days at a dose of one drop in a single eye for a total daily dose of about 0.035 mg. In some aspects, the formulation is administered on one or more consecutive days at a dose of one drop in each eye for a total daily dose of about 0.07 mg of oxymetazoline hydrochloride.

In one aspect, the pharmaceutical composition is administered once daily to one or both eyes. In one aspect, the pharmaceutical composition is administered in the morning. In one aspect, the pharmaceutical composition is administered in the afternoon. In one aspect, the pharmaceutical composition is administered in the evening. In one aspect, the pharmaceutical composition is administered more than 4 hours before bedtime. In some aspects, a pharmaceutical composition containing oxymetazoline or a pharmaceutically acceptable salt thereof, is administered twice per day or once per day in a unit dose comprising about 0.015 mg, about 0.035 mg, or about 0.07 mg. In some aspects, a single drop is administered to each eye during each dose administration. In some aspects, a single drop is administered to only one eye during each dose administration.

VI. Pharmaceutical Compositions

Another aspect of the present disclosure relates to a pharmaceutical composition comprising oxymetazoline hydrochloride. For ophthalmic application, preferably solutions are prepared using a physiological saline solution as the vehicle. The pH of such ophthalmic solutions should preferably be maintained from 4.5 and 8.0 with an appropriate buffer system. Ideally, the pH of such solutions is maintained from 6.3 and 6.5. The formulations can also contain conventional, pharmaceutically acceptable stabilizers and surfactants. Tonicity adjustors can be added as needed or convenient. They include, but are not limited to, salts, particularly sodium chloride, potassium chloride, mannitol and glycerin, or any other suitable ophthalmically acceptable tonicity adjustor. Various buffers and means for adjusting pH can be used so long as the resulting preparation is ophthalmically acceptable. Accordingly, buffers include acetate buffers, citrate buffers, phosphate buffers and borate buffers. In some aspects, the pharmaceutical composition is an ophthalmic dosage form. The present disclosure is not limited to a particular ophthalmic dosage form, and any dosage form capable of delivering oxymetazoline hydrochloride to a patient is suitable for the present invention, so long as the dosage form achieves pharmacokinetic and therapeutic effects described in the present disclosure.

In one aspect, the formulation does not contain preservative(s).

In some aspects, the pharmaceutical composition comprises an adsorbent, antioxidant, buffering agent, and/or diluent.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium citrate, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

VII. Leicester Peripheral Field Test (LPFT)

The efficacy of the compositions of the present disclosure can be evaluated using a variety of tests to assess patient improvement. In some aspects, a Leicester Peripheral Field Test (LPFT) is used to assess patient improvement outcomes. In some aspects, a Leicester Peripheral Field Test (LPFT) is used for assessment, and a Leicester Peripheral Field Test (LPFT) mean score and a Leicester Peripheral Field Test (LPFT) median score is determined. In some aspects, the Leicester Peripheral Field Test (LPFT) mean score is increased by about 5-10 points after about 0.1-16 hours. In some aspects, the Leicester Peripheral Field Test (LPFT) mean score is increased by about 5.2 points or about 6.3 points after about 0.1-16 hours. In some aspects, the Leicester Peripheral Field Test (LPFT) mean score is increased by about 5.2 points or about 6.3 points after about 6 hours. In some aspects, the Leicester Peripheral Field Test (LPFT) mean score is increased by about 5-10 points after about 10-15 days. In some aspects, the Leicester Peripheral Field Test (LPFT) mean score is increased by about 6 points to about 8 points after about 10-15 days. In some aspects, the Leicester Peripheral Field Test (LPFT) mean score is increased by about 6.4 points or about 7.7 points after about 10-15 days. In some aspects, the Leicester Peripheral Field Test (LPFT) mean score is increased by about 6.4 points or about 7.7 points after about 14 days.

In some aspects, the Leicester Peripheral Field Test (LPFT) mean score is increased by about 5-10 points after about 0.1-16 hours. In some aspects, the Leicester Peripheral Field Test (LPFT) mean score is increased by about 5-10 points after about 5 to about 10 minutes. In some aspects, the Leicester Peripheral Field Test (LPFT) mean score is increased by about 5.2 points or about 6.3 points after about 0.1-16 hours. In some aspects, the Leicester Peripheral Field Test (LPFT) mean score is increased by about 5.2 points or about 6.3 points after about 6 hours. In some aspects, the Leicester Peripheral Field Test (LPFT) mean score is increased by about 5.2 points after about 6 hours. In some aspects, the Leicester Peripheral Field Test (LPFT) mean score is increased by about 6.3 points after about 6 hours. In some aspects, the Leicester Peripheral Field Test (LPFT) mean score is increased by about 7.7 points after about 2 hours. In some aspects, the Leicester Peripheral Field Test (LPFT) mean score is increased by about 6.4 points after about 2 hours. In some aspects, the Leicester Peripheral Field Test (LPFT) mean score is increased by about 5-10 points after about 10-15 days. In some aspects, the Leicester Peripheral Field Test (LPFT) mean score is increased by about 6 points to about 8 points after about 10-15 days. In some aspects, the Leicester Peripheral Field Test (LPFT) mean score is increased by about 6.4 points or about 7.7 points after about 10-15 days. In some aspects, the Leicester Peripheral Field Test (LPFT) mean score is increased by about 6.4 points or about 7.7 points after about 14 days.

In some aspects, the Leicester Peripheral Field Test (LPFT) median score is increased by about 5-10 points after about 0.1-16 hours. In some aspects, the Leicester Peripheral Field Test (LPFT) median score is increased by about 7 points after about 0.1-16 hours. In some aspects, a Leicester Peripheral Field Test (LPFT) is used for assessment, and a Leicester Peripheral Field Test (LPFT) mean score and a Leicester Peripheral Field Test (LPFT) median score is determined. In some aspects, the Leicester Peripheral Field Test (LPFT) median score is increased by about 5-10 points after about 2 hours or after about 6 hours. In some aspects, the Leicester Peripheral Field Test (LPFT) median score is increased by about 7 points after about 6 hours. In some aspects, the Leicester Peripheral Field Test (LPFT) median score is increased by about 5-10 points after about 10-15 days. In some aspects, the Leicester Peripheral Field Test (LPFT) median score is increased by about 9 points after about 10-15 days. In some aspects, the Leicester Peripheral Field Test (LPFT) median score is increased by about 9 points after about 14 days.

In some aspects, the Leicester Peripheral Field Test (LPFT) mean score is increased by about 5-20 points after about 1-9 hours. In some aspects, the Leicester Peripheral Field Test (LPFT) mean score is increased by about 5-15 points after about 0.1-16 hours. In some aspects, the Leicester Peripheral Field Test (LPFT) mean score is increased by about 10-15 points after about 0.1-16 hours. In some aspects, the Leicester Peripheral Field Test (LPFT) mean score is increased by about 5-15 points after about 2 to about 6 hours. In some aspects, the Leicester Peripheral Field Test (LPFT) mean score is increased by about 5-15 points after about 1-14 days. In some aspects, the Leicester Peripheral Field Test (LPFT) mean score is increased by about 5-10 points after about 1 day. In some aspects, the Leicester Peripheral Field Test (LPFT) mean score is increased by about 5-10 points after about 14 days. In some aspects, the Leicester Peripheral Field Test (LPFT) mean score is increased by about 5-10 points after about 14 days. In some aspects, the Leicester Peripheral Field Test (LPFT) mean score is increased by about 5-10 points after about 0.1-16 hours.

In some aspects, the Leicester Peripheral Field Test (LPFT) mean score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 0.1-16 hours. In some aspects, the Leicester Peripheral Field Test (LPFT) mean score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 6 hours. In some aspects, the Leicester Peripheral Field Test (LPFT) mean score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 10-15 days. In some aspects, the Leicester Peripheral Field Test (LPFT) mean score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20, points after about 14 days.

In some aspects, the Leicester Peripheral Field Test (LPFT) median score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 0.1-16 hours. In some aspects, the Leicester Peripheral Field Test (LPFT) median score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 6 hours. In some aspects, the Leicester Peripheral Field Test (LPFT) median score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 10-15 days. In some aspects, the Leicester Peripheral Field Test (LPFT) median score is increased by about 1, by about 2, by about 3, by about 4, by about 5, by about 6, by about 7, by about 8, by about 9, by about 10, by about 11, by about 12, by about 13, by about 14, by about 15, by about 16, by about 17, by about 18, by about 19, or by about 20 points after about 14 days.

In some aspects, the Leicester Peripheral Field Test (LPFT) median score remains elevated for a period of about 10 minutes, about 20 minutes, about 1 hour, about 6 hours, about 8 hours, about 12 hours, or about 24 hours.

VIII. Marginal Reflex Distance 1 (MRD-1) Test

The Marginal Reflex Distance 1 (MRD-1) test is conducted using photographic measurement to assess the distance from the central pupillary light reflex to the central margin of the upper lid. External digital photographs are used to measure MRD-1. Measurements are taken based on the distance from the central pupillary light reflex to the central margin of the upper lid, ≤2 mm (no visible central pupillary light reflex defaults to 0). The MRD-1 test is useful to assess efficacy of treatment.

In some aspects, a Marginal Reflex Distance 1 Test (MRD-1) is used to assess patient improvement outcomes. In some aspects, a Marginal Reflex Distance 1 Test (MRD-1) is used for assessment, and a Marginal Reflex Distance 1 Test (MRD-1) mean score and a Marginal Reflex Distance 1 Test (MRD-1) median score is determined. In some aspects, a Marginal Reflex Distance 1 Test (MRD-1) is conducted, and whereby the mean score is increased by about 0.2-1.0 points after about 1-10 minutes. In some aspects, the Marginal Reflex Distance 1 Test (MRD-1) mean score is increased by about 0.2-1.0 points after about 5 minutes. In some aspects, the Marginal Reflex Distance 1 Test (MRD-1) mean score is increased by about 0.6 points after about 5 minutes. In some aspects, the Marginal Reflex Distance 1 Test (MRD-1) mean score is increased by about 0.5-1.5 points after about 10-20 minutes. In some aspects, the Marginal Reflex Distance 1 Test (MRD-1) mean score is increased by about 0.5-1.5 points after about 15 minutes. In some aspects, the Marginal Reflex Distance 1 Test (MRD-1) mean score is increased by about 0.9 points after about 15 minutes.

In some aspects, the Marginal Reflex Distance 1 Test (MRD-1) mean score is increased by about 0.5-1.5 points after about 5 minutes to about 16 hours. In some aspects, the Marginal Reflex Distance 1 Test (MRD-1) mean score is increased by about 0.5-1.5 points after about 15 minutes to about 16 hours. In some aspects, the Marginal Reflex Distance 1 Test (MRD-1) mean score is increased by about 0.5-1.5 points after about 15 minutes. In some aspects, the mean score is increased by about 0.2-1.0 points after about 5 minutes to about 16 hours. In some aspects, the mean score is increased by about 0.5-1.5 points after about 5 minutes to about 42 days.

In some aspects, the Marginal Reflex Distance 1 Test (MRD-1) mean score is increased by about 1.5 points, by about 1.4 points, by about 1.3 points, by about 1.2 points, by about 1.1 points, by about 1.0 point, by about 0.9 points, by about 0.8 points, by about 0.7 points, by about 0.6 points, by about 0.5 points, by about 0.4 points, or by about 0.3 points after about 5 minutes to about 16 hours. In some aspects, the Marginal Reflex Distance 1 Test (MRD-1) mean score is increased by about 1.5 points, by about 1.4 points, by about 1.3 points, by about 1.2 points, by about 1.1 points, by about 1.0 point, by about 0.9 points, by about 0.8 points, by about 0.7 points, by about 0.6 points, by about 0.5 points, by about 0.4 points, or by about 0.3 points after about 5 minutes. In some aspects, the Marginal Reflex Distance 1 Test (MRD-1) mean score is increased by about 1.5 points, by about 1.4 points, by about 1.3 points, by about 1.2 points, by about 1.1 points, by about 1.0 point, by about 0.9 points, by about 0.8 points, by about 0.7 points, by about 0.6 points, by about 0.5 points, by about 0.4 points, or by about 0.3 points after about 15 minutes. In some aspects, the Marginal Reflex Distance 1 Test (MRD-1) mean score is increased by about 1.5 points, by about 1.4 points, by about 1.3 points, by about 1.2 points, by about 1.1 points, by about 1.0 point, by about 0.9 points, by about 0.8 points, by about 0.7 points, by about 0.6 points, by about 0.5 points, by about 0.4 points, or by about 0.3 points after about 16 hours.

In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 1-20 minutes. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 5 minutes.

In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 10-20 minutes. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 15 minutes.

In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 2-12 hours. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 2 hours. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 6 hours.

In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 5-20 days. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 14 days.

In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 30-60 days. In some aspects, the Marginal Reflex Distance 1 (MRD-1) mean score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 42 days.

In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 1-20 minutes. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 0.1-16 hours, e.g., 8 hours. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 5 minutes.

In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 10-20 minutes. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 15 minutes.

In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 2-12 hours. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 2 hours. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 6 hours.

In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 5-20 days. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 14 days.

In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 30-60 days. In some aspects, the Marginal Reflex Distance 1 (MRD-1) median score is increased by about 0.1, by about 0.2, by about 0.3, by about 0.4, by about 0.5, by about 0.6, by about 0.7, by about 0.8, by about 0.9, by about 1.0, by about 1.1, by about 1.2, by about 1.3, by about 1.4, by about 1.5, by about 1.6, by about 1.7, by about 1.8, by about 1.9, or by about 2.0 points after about 42 days.

IX. Pharmacokinetics

In one aspect, the dose comprises two drops of about 0.035 g/drop of a 0.1 wt % composition for a total dose of about 0.070 mg and wherein the pharmaceutical composition comprises about 0.035 mg oxymetazoline hydrochloride in each drop. In another aspect, each drop of ophthalmic solution contains 0.035 mg (0.1% oxymetazoline hydrochloride, which is equivalent to 0.031 mg (0.088% of oxymetazoline free base equivalents).

The compositions and methods of the present disclosure are useful for minimizing a patient's systemic exposure to oxymetazoline hydrochloride. In some aspects, a mean $AUC_{0-\infty}$ of the pharmaceutical composition after a single-dose administration is from about 300 to about 700 pg·h/mL. In some aspects, a mean $AUC_{0-\infty}$ of the pharmaceutical composition after a single-dose administration is about 468 pg·h/mL.

In some aspects, the $T_{max}$ of the pharmaceutical composition after a single-dose administration is from about 0.5 to about 6 hours. In some aspects, the $T_{max}$ of the pharmaceutical composition after a single-dose administration is about 2-4 hours. In some aspects, the $T_{max}$ of the pharmaceutical composition after a single-dose administration is about 0.5-4 hours. In some aspects, the $T_{max}$ of the pharmaceutical composition after a single-dose administration is about 2 hours.

In some aspects, the mean $T_{max}$ of the pharmaceutical composition after single dose administration to a patient is from about 0.5 hours to about 12 hours, from about 0.5 hours to about 10 hours, from about 0.5 hours to about 8 hours, from about 0.5 hours to about 6 hours, from about 6 hours to about 12 hours, from about 6 hours to about 10 hours, from about 6 hours to about 8 hours, from about 7 hours to about 12 hours, from about 7 hours to about 10 hours, from about 7 hours to about 8 hours, from about 8 hours to about 12 hours, from about 8 hours to about 10 hours, from about 9 hours to about 12 hours, from about 9 hours to about 10 hours, or from about 10 hours to about 12 hours. In some aspects, the mean $T_{max}$ of the pharmaceutical composition is from about 0 hours to about 6 hours, from about 1 hours to about 6 hours, from about 1 hours to about 5 hours, from about 2 hours to about 5 hours, from about 2 hours to about 4 hours, or from about 2 hours to about 3 hours. In one aspect, the mean $T_{max}$ of the pharmaceutical composition is about 2.5 hours. In some aspects, the median $T_{max}$ of the pharmaceutical composition is about 1 hour, about 2 hours, about 3 hours, about 4 hours, about 5 hours, about 6 hours, about 7 hours, about 8 hours, about 9 hours, or about 10 hours.

In some aspects, the mean $C_{max}$ of the pharmaceutical composition after a single-dose administration is from about 25 pg/ml to about 35 pg/ml. In some aspects, the mean $C_{max}$ of the pharmaceutical composition after a single-dose administration is about 28-32 pg/ml. In some aspects, the mean $C_{max}$ of the pharmaceutical composition after a single-dose administration is about 30.5 pg/ml.

In one aspect, the dose comprises two drops of about 0.035 g/drop of a 0.1 wt % composition for a total of about 0.070 g and wherein the pharmaceutical composition comprises about 0.035 mg oxymetazoline hydrochloride in each drop. In some aspects, the mean $C_{max}$ of the pharmaceutical composition after a single-dose administration to a patient is from about 10 pg/ml to about 40 pg/ml, from about 12 pg/ml to about 38 pg/ml, from about 14 pg/ml to about 36 pg/ml, from about 16 pg/ml to about 34 pg/ml, from about 18 pg/ml to about 32 pg/ml, or from about 20 pg/ml to about 30 pg/ml. In some aspects, the mean $C_{max}$ of the pharmaceutical composition after a single-dose administration is about 20 pg/ml, about 21 pg/ml, about 22 pg/ml, about 22 pg/ml, about 23 pg/ml, about 24 pg/ml, about 25 pg/ml, about 26 pg/ml, about 27 pg/ml, about 28 pg/ml, about 29 pg/ml, about 30 pg/ml, about 31 pg/ml, about 32 pg/ml, about 33 pg/ml, about 34 pg/ml, about 35 pg/ml, about 36 pg/ml, about 37 pg/ml, about 38 pg/ml, about 39 pg/ml, or about 40 pg/ml. In some aspects, the mean $C_{max}$ of the pharmaceutical composition after a single-dose administration is from about 25 pg/ml to about 35 pg/ml. In some aspects, the mean $C_{max}$ of the pharmaceutical composition after a single-dose administration is about 28-32 pg/ml. In some aspects, the mean $C_{max}$ of the pharmaceutical composition after a single-dose administration is about 30.5 pg/ml. In some aspects, the mean $C_{max}$ of the pharmaceutical composition after a single-dose administration is about 30.5 pg/ml, and the geometric mean $C_{max}$ is about 28.3 pg/mL.

In some aspects, the mean area under the plasma concentration-time curve ($AUC_{0-\infty}$) is measured. In some aspects, a mean $AUC_{0-\infty}$ of the pharmaceutical composition after a single-dose administration is from about 0 pg·h/mL to about 800 pg·h/mL, from about 50 pg·h/mL to about 800 pg·h/mL, from about 50 pg·h/mL to about 750 pg·h/mL, from about 100 pg·h/mL to about 750 pg·h/mL, from about 100 pg·h/mL to about 700 pg·h/mL, from about 150 pg·h/mL to about 700 pg·h/mL, from about 150 pg·h/mL to about 650 pg·h/mL, from about 200 pg·h/mL to about 650 pg·h/mL, from about 200 pg·h/mL to about 600 pg·h/mL, from about 250 pg·h/mL to about 600 pg·h/mL, from about 250 pg·h/mL to about 550 pg·h/mL, from about 300 pg·h/mL to about 550 pg·h/mL, from about 300 pg·h/mL to about 500 pg·h/mL, from about 350 pg·h/mL to about 500 pg·h/mL, from about 400 pg·h/mL to about 500 pg·h/mL, or from about 420 pg·h/mL to about 480 pg·h/mL. In some aspects, a mean $AUC_{0-\infty}$ of the pharmaceutical composition after a single-dose administration is about 468 pg·h/mL.

In some aspects, the geometric mean $AUC_{0-\infty}$ of the pharmaceutical composition after a single-dose administration is from about 0 pg·h/mL to about 800 pg·h/mL, from about 50 pg·h/mL to about 800 pg·h/mL, from about 50 pg·h/mL to about 750 pg·h/mL, from about 100 pg·h/mL to about 750 pg·h/mL, from about 100 pg·h/mL to about 700 pg·h/mL, from about 150 pg·h/mL to about 700 pg·h/mL, from about 150 pg·h/mL to about 650 pg·h/mL, from about 200 pg·h/mL to about 650 pg·h/mL, from about 200 pg·h/mL to about 600 pg·h/mL, from about 250 pg·h/mL to about 600 pg·h/mL, from about 250 pg·h/mL to about 550 pg·h/mL, from about 300 pg·h/mL to about 550 pg·h/mL, from about 300 pg·h/mL to about 500 pg·h/mL, from about 350 pg·h/mL to about 500 pg·h/mL, from about 400 pg·h/mL to about 500 pg·h/mL, or from about 420 pg·h/mL to about 480 pg·h/mL. In some aspects, the geometric mean $AUC_{0-\infty}$ of the pharmaceutical composition after a single-dose administration is about 439 pg·h/mL.

X. Packaging

The storage format and packaging of a formulation is also important to maintain and deliver consistent product. The packaging methods of the present disclosure can involve the use of a single unit-dose container formed from clear, low-density polyethylene (LDPE) resin. In some aspects, the single-use containers are formed by a blow/fill/seal ("B/F/S" or "BFS") process. In some aspects, the BFS process is performed in an aseptic environment. The BFS process is a process where the container is formed, filled, and sealed in one continuous, automated system, wherein contents are kept sterile. The BFS vials are continuously produced on a machine that extrudes the plastic resin at high temperature, rendering the resin sterile. The pellets feed from the hopper at the top of the BFS machine into the extruder via gravity. The extruder heats the resin pellets to about 170° C. to about 230° C., melting the plastic granulate to produce a sterile, extruded plastic tube (parison). The process begins by melting and extruding the low density polyethylene (LDPE) resin to form a parison (a hollow tubular form of the hot resin). Then the seal molds close, sealing the vials, and the molds release the filled and sealed vials. The entire process is conducted without human intervention, thus reducing the risk of contamination. The BFS vials can be filled upside down to ensure consistent filling and sealed to form a "card" containing multiple vials. Sterile packaging techniques are important when the content does not contain preservatives or anti-microbial agents. In some aspects, the BFS vial has a volume of about 0.1 mL, about 0.2 mL, about 0.3 mL, about 0.4 mL, about 0.5 mL, about 0.6 mL, about 0.7 mL, about 0.8 mL, about 0.9 mL, or about 1.0 mL. In some aspects, the BFS vial has a volume of about 1 mL, about 2 mL, about 3 mL, about 4 mL, about 5 mL, about 6 mL, about 7 mL, about 8 mL, about 9 mL, or about 10 mL. In some aspects, the BFS vial has a volume of about 0.5 mL. In some aspects, the BFS vial has a volume of 0.34 mL.

After BFS packaging, the containers can be enclosed in a foil laminate pouch for individual packaging, and/or enclosed in a child-resistant zipper bag to prevent unwanted access. Pharmaceuticals generally require product packaging compliant with government regulations to include child-resistant features to prevent young children, e.g., age 5 or younger, from gaining access to products that could cause serious illness or injury. Alternatively, the containers can be enclosed in a child-resistant foil laminate pouch. The child-resistant pouching materials can comprise PET, aluminum foil, and/or sealant that can provide puncture resistance, machinability, integrity, and child resistance.

The present disclosure is further illustrated by the following examples which should not be construed as further limiting. The contents of all references cited throughout this application are expressly incorporated herein by reference.

EXAMPLES

Example 1

Formulation

The oxymetazoline hydrochloride ophthalmic solution, 0.1 wt %, was manufactured at a batch size of 200 kg. The batch formula for the drug product is provided in Table 1.

TABLE 1

Batch Formula for Oxymetazoline HCl Ophthalmic Solution, 0.1 wt %

| Component | Quality Standard | Function | Quantity per batch | Quantity (mg/mL) | Quantity (mg/dosage unit) |
|---|---|---|---|---|---|
| Oxymetazoline Hydrochloride | USP | Active | 200.00 g* | 1.00 | 0.34 |
| Sodium Chloride | USP | Excipient | 1280.00 g | 6.40 | 2.18 |
| Potassium Chloride | USP | Excipient | 150.00 g | 0.75 | 0.26 |
| Calcium Chloride, Dihydrate | USP | Excipient | 96.00 g | 0.48 | 0.16 |
| Magnesium Chloride Hexahydrate | USP | Excipient | 60.00 g | 0.30 | 0.10 |
| Sodium Acetate Trihydrate | USP | Excipient | 780.00 g | 3.90 | 1.33 |
| Sodium Citrate | NF | Excipient | 340.00 g | 1.70 | 0.58 |
| Hypromellose** (Methocel E4M) | USP | Excipient | 1000.00 g | 5.00 | 1.70 |
| Hydrochloric Acid | NF | pH Adjuster | 25 mL | To adjust pH to 6.3-6.5 | To adjust pH to 6.3-6.5 |
| Water for Injection | USP | Diluent | QS to 200 kg | QS | QS to 0.34 mL |
| Nitrogen (sterile filtered) | NF | Filling and Support Gas | N/A | N/A | N/A |

*Adjusted based on Assay value
**Adjust to compensate for a 5 kg purge

Formulation enhancements were pursued in an attempt to improve the overall absorption of oxymetazoline within the eye, without the use of preservatives. The vehicle formulation is a balanced salt solution intended for eye irrigation that is made to a physiological pH and isotonic salt concentration. Addition of the excipient hypromellose, which is a viscosity modifier, helps add residence time in the eye, as well as enhance eye comfort. Eight development batches were tested using either Hypromellose (HPMC) or Sodium Carboxymethyl-cellulose (NA CMC). The effect of this change on pH was determined as well. Stability studies were conducted at 25° C.±2° C./40% RH, 40° C.±2° C./NMT 25% RH, and 55° C./Ambient RH. The compositions and results of these tests, including 3-month stability test data, can be seen in Table 2 and Table 3 below:

TABLE 2

Composition (% w/w) of the Eight Development Batches (batch sizes ~91-172 g)

| Ingredient | Lot EPS-352-057 | Lot EPS-352-059 | Lot EPS-352-060 | Lot EPS-352-061 | Lot EPS-352-062 | Lot EPS-352-065 | Lot EPS-357-036 | Lot EPS-357-039 |
|---|---|---|---|---|---|---|---|---|
| Sodium Chloride | 0.64% | 0.64% | 0.64% | 0.64% | 0.64% | 0.64% | 0.64% | 0.64% |
| Potassium Chloride | 0.075% | 0.075% | 0.075% | 0.075% | 0.075% | 0.075% | 0.075% | 0.075% |
| Calcium Chloride | 0.048% | 0.048% | 0.048% | 0.048% | 0.048% | 0.048% | 0.048% | 0.048% |
| Magnesium Chloride | 0.030% | 0.030% | 0.030% | 0.030% | 0.030% | 0.030% | 0.030% | 0.030% |
| Sodium acetate | 0.39% | 0.39% | 0.39% | 0.39% | 0.39% | 0.39% | 0.39% | 0.39% |
| Sodium citrate | 0.17% | 0.17% | 0.17% | 0.17% | 0.17% | 0.17% | 0.17% | 0.17% |
| HPMC (Hypromellose) | — | 1.0% | — | 0.5% | — | — | — | — |
| Sodium Carboxymethyl-cellulose | 1.0% | — | 0.5% | — | 0.25% | 0.25% | 0.25% | 0.25% |
| pH | 7.2 | 7.2 | 7.2 | 7.2 | 5.5 | 6.0 | 6.5 | 7.0 |
| Water for Injection | q.s. | q.s. | q.s. | q.s. | q.s. | q.s. | q.s. | q.s. |

TABLE 3

Initial Data on the Eight Developmental Batches (batch size ~91-172 g)

| Formulation ID | Concentration of Oxymetazoline (mg/mL) | pH | Osmolality (mOsm/kg) | Concentration of Oxymetazoline (mg/mL) 3-Month Stability Test at 25° C. ± 2° C./ 40% RH | Concentration of Oxymetazoline (mg/mL) 3-Month Stability Test at 40° C. ± 2° C./ NMT 25% RH |
|---|---|---|---|---|---|
| EPS-352-057 (1% Na CMC) | 0.99 | 6.6 | 326 | 0.99 | 0.97 |
| EPS-352-059 (1% HPMC) | 0.90 | 6.5 | 314 | 0.94 | 0.91 |
| EPS-352-060 (0.5% Na CMC) | 0.99 | 6.5 | 313 | 0.98 | 0.99 |
| EPS-352-061 (0.5% HPMC) | 0.95 | 6.5 | 308 | 0.96 | 0.95 |
| EPS-352-062 (0.25% Na CMC; pH 5.5) | 0.97 | 5.6 | 301 | 0.98 | 1.00 |
| EPS-352-065 (0.25% Na CMC; pH 6.0) | 0.99 | 5.8 | 309 | 0.99 | 1.00 |
| EPS-357-036 (0.25% Na CMC; pH 6.5) | 0.97 | 6.0 | 302 | 0.98 | 0.95 |
| EPS-357-039 (0.25% Na CMC; pH 7.0) | 1.00 | 6.6 | 305 | 0.99 | 0.97 |

Example 2

PK Analysis

The following pharmacokinetic data was generated based on a single drop dose in each eye, each drop containing approximately 0.035 mg of oxymetazoline HCl, for a total of 0.07 mg oxymetazoline HCl.

Parameters $C_{max}$, $AUC_{0-\infty}$, and $T_{max}$ were assessed based on a test population of 24 patients.

A study was conducted to determine mean plasma oxymetazoline concentrations following single-dose administration of Oxymetazoline HCl Ophthalmic Solution, 0.1 wt %. The results of the study are detailed in FIG. 1, Table 4, and Table 5.

TABLE 4

Summary of Pharmacokinetic Parameters Following Ocular Administration of Oxymetazoline to Healthy Male and Female Volunteers, PK Study

| Parameter | n | Test Mean | Test SD | Test CV % | Geometric Mean |
|---|---|---|---|---|---|
| tmax(h)[a] | 23 | 2.00 (0.500-12.0) | | | — |
| Cmax (pg/mL) | 23 | 30.5 | 12.7 | 41.8 | 28.3184 |
| AUC0-tldc (h*pg/mL) | 23 | 400 | 188 | 47.1 | 367.5829 |
| AUCinf (h*pg/mL) | 19 | 468 | 214 | 45.7 | 438.9934 |
| AUC % extrap | 21 | 12.4 | 5.41 | 43.7 | — |
| kel (h-1) | 21 | 0.0841 | 0.0190 | 22.6 | — |
| t½ (h)[b] | 21 | 8.25 | — | — | — |

Treatment A: one drop of oxymetazoline HCl (ophthalmic solution, 0.1 wt %) to each eye (Test)

Note:

PK parameters are presented as arithmetic mean, standard deviation (SD), and coefficient of variation (CV %) unless otherwise noted.

AUCinf values with extrapolation >20% were excluded from summary statistics.

[a]tmax is presented as median (min-max)

[b]t½ is presented as harmonic mean

TABLE 5

Summary of Oxymetazoline Concentration-Time Data Following Single-Dose Administration of Oxymetazoline HCl ophthalmic Solution, 0.1%; Treatment A

| Treatment | Time (h) | n | Mean (pg/mL) | SD (pg/mL) | CV % | Min (pg/mL) | Median (pg/mL) | Max (pg/mL) |
|---|---|---|---|---|---|---|---|---|
| A | 0.00 | 23 | 0.00 | 0.00 | NC | 0.00 | 0.00 | 0.00 |
| | 0.17 | 23 | 11.6 | 6.45 | 55.4 | 4.64 | 11.1 | 29.4 |
| | 0.33 | 23 | 16.4 | 7.51 | 45.8 | 4.44 | 14.1 | 32.5 |
| | 0.50 | 23 | 18.8 | 7.02 | 37.4 | 8.73 | 18.1 | 33.5 |
| | 0.75 | 23 | 19.7 | 7.05 | 35.7 | 9.91 | 17.9 | 34.8 |
| | 1.00 | 23 | 20.2 | 7.90 | 39.1 | 9.37 | 17.6 | 39.0 |
| | 1.50 | 23 | 23.3 | 10.8 | 46.4 | 7.15 | 21.8 | 54.7 |
| | 2.00 | 23 | 23.0 | 8.27 | 35.9 | 7.82 | 23.8 | 48.6 |
| | 3.00 | 23 | 24.4 | 9.25 | 37.9 | 8.54 | 23.6 | 50.0 |
| | 4.00 | 23 | 25.8 | 12.3 | 47.7 | 9.87 | 21.5 | 51.8 |
| | 6.00 | 23 | 22.7 | 11.7 | 51.4 | 9.12 | 17.9 | 58.4 |
| | 8.00 | 23 | 19.7 | 10.2 | 51.5 | 9.01 | 18.3 | 50.6 |
| | 12.00 | 23 | 13.8 | 7.42 | 53.9 | 6.40 | 12.6 | 39.0 |
| | 16.00 | 23 | 11.3 | 6.88 | 60.7 | 4.36 | 10.1 | 35.2 |
| | 24.00 | 23 | 6.37 | 4.75 | 74.5 | 0.00 | 5.76 | 21.9 |
| | 30.00 | 23 | 3.36 | 3.44 | 102 | 0.00 | 3.36 | 12.9 |
| | 36.00 | 23 | 1.21 | 2.35 | 195 | 0.00 | 0.00 | 9.01 |

Example 3

Phase 3 Data, Study 1

Study 1: This Study was a multicenter, randomized, double-masked, placebo-controlled, Phase 3 study of the safety and efficacy of once per day dosing (QD) treatment (one drop per eye) with oxymetazoline hydrochloride ophthalmic solution, 0.1% compared to Vehicle in subjects with acquired ptosis. A total of 140 subjects were randomized in an approximate 2:1 ratio: oxymetazoline hydrochloride 0.1 wt % QD (N=94); Vehicle (N=46) at 16 sites. Oxymetazoline hydrochloride was administered topically for 42 days (6 weeks). The study was conducted in 2 periods; Period 1 (safety and efficacy) was 2 weeks in duration, and Period 2 (extended safety and comfort) was 4 weeks in duration. The mean age of the subjects was 64.2 years.

3.2 Efficacy

Efficacy was assessed with the LPFT (primary) and photographic measurement of MRD-1. The primary efficacy endpoints were ordered in a hierarchy to compare oxymetazoline hydrochloride against vehicle on the mean increase from baseline (Day 1 Hour 0) in the number of points seen on the top 4 rows of the LPFT in the study eye at:
1. Hour 6 on Day 1
2. Hour 2 on Day 14

This study has been completed and the results are presented below. The increases at both time points in the number of points seen in the superior visual field (change in LPFT) in the oxymetazoline hydrochloride group compared to the Vehicle group were statistically significant, showing that the improvement in the superior visual field was evident at 6 hours post-dose on Day 1 and 2 hours post-dose on Day 14, Table 6. The mean change from baseline for the visual field data at time points Day 14, hour 6, Day 14, hour 8, and Day 42 can be seen in Table 7.

TABLE 6

Observed and Change from Baseline in Mean Points Seen in Superior Visual Field on LPFT in the Study Eye at Primary Efficacy Time Points (ITT Population), Study 1

| Parameter | Points Seen in Superior Visual Field | | Mean Difference, P-Value$^a$ [95% CI] P-Value$^b$ Test vs Vehicle |
|---|---|---|---|
| | Test N = 94 | Vehicle N = 46 | |
| Mean points at baseline (SD) | 17 (4.41) | 1 (5.21) | — |
| N Day 1, Hour 6, observed mean (SD) | 94 22.2 (6.18) | 46 18.4 (6.01) | |
| Mean change from baseline (SD) | 5.2 (5.97) | 1.5 (3.93) | 3.67, <0.0001$^a$, [2.00, 5.34] 0.0002$^b$ |
| N Day 14, Hour 2, observed mean (SD) | 91 23.4 (5.60) | 46 19.1 (6.13) | |
| Mean change from baseline (SD) | 6.4 (5.04) | 2.2 (5.80) | 4.20, <0.0001$^a$, [2.30, 6.10] <0.0001$^b$ |

CI = confidence interval;
ITT = intent-to-treat;
LPFT = Leicester Peripheral Field Test;
SD = standard deviation
$^a$P-value = 2-sided t-test
$^b$P-value = Wilcoxon test

TABLE 7

Mean Change from Baseline in Marginal Reflex Distance 1 in the Study Eye (ITT Population), Study 1

| Parameter | Test N = 94 | Vehicle N = 46 | Mean Difference, P-Value$^a$ [95% CI] P-Value$^b$ Test vs Vehicle |
|---|---|---|---|
| Mean MRD-1 at baseline, mm (SD) | 1.16 (0.661) | 1.03 (0.678) | — |
| Mean change from baseline in MRD-1 at primary efficacy time points, mm (SD) | | | |
| Day 1, Hour 6 | n = 94 0.94 (0.924) | n = 46 0.67 (1.001) | 0.27, 0.1198$^a$, [−0.07, 0.61] 0.0276$^b$ |
| Day 14, Hour 2 | n = 91 1.09 (0.799) | n = 46 0.58 (0.875) | 0.52, 0.0007$^a$, [0.22, 0.81] 0.0004$^b$ |
| Mean change from baseline in MRD-1 at remaining post-dosing time points, mm (SD) | | | |
| Day 1, Hour 2 | n = 94 0.99 (0.776) | n = 46 0.50 (0.803) | 0.49, 0.0007$^a$, [0.21, 0.77] <0.0001$^b$ |
| Day 1, Hour 8 | n = 94 0.93 (0.958) | n = 46 0.70 (0.771) | 0.24, 0.1491$^a$, [−0.09, 0.56] 0.1701$^b$ |
| Day 14, Hour 6 | n = 92 1.03 (0.856) | n = 45 0.70 (0.985) | 0.33, 0.0477$^a$, [0.00, 0.65] 0.0101$^b$ |
| Day 14, Hour 8 | n = 91 0.88 (0.857) | n = 45 0.68 (1.023) | 0.20, 0.2295$^a$ [−0.13, 0.53] 0.1511$^b$ |
| Day 42 | n = 91 1.25 (1.036) | n = 45 0.79 (1.020) | 0.46, 0.0160$^a$, [0.09, 0.83] 0.0113$^b$ |

CI = confidence interval;
ITT = intent-to-treat;
MRD −1 = marginal reflex distance −1;
SD = standard deviation
$^a$P-value = 2-sided t-test
$^b$P-value = Wilcoxon test

Example 4

Phase 3 Data, Study 2

Study 2: This Study was a multicenter, randomized, double-masked, placebo-controlled, Phase 3 study of the safety and efficacy of once per day dosing (QD) treatment (one drop per eye) with oxymetazoline hydrochloride compared to Vehicle in subjects with acquired ptosis. A total of 164 subjects were randomized in an approximate 2:1 ratio: oxymetazoline hydrochloride 0.1 wt % QD (N=109); Vehicle (N=55) at 27 sites. Oxymetazoline hydrochloride 0.1 wt % was administered topically for 42 days (6 weeks). The study was conducted in 2 periods; Period 1 (safety and efficacy) was 2 weeks in duration, and Period 2 (extended safety and comfort) was 4 weeks in duration. The mean age of the subjects was 63.5 years. One subject was younger than 18 years old.

4.1 Efficacy

Efficacy was assessed with the LPFT (primary) and photographic measurement of MRD-1. The primary efficacy endpoints were ordered in a hierarchy to compare oxymetazoline hydrochloride against vehicle on the mean increase from baseline (Day 1 Hour 0) in the number of points seen on the top 4 rows of the LPFT in the study eye at:

1. Hour 6 on Day 1
2. Hour 2 on Day 14

The results are presented below. The increases at both time points in the number of points seen in the superior visual field (change in LPFT) in the oxymetazoline hydrochloride group compared to the Vehicle group were statistically significant, showing that the improvement in the superior visual field was evident at 6 hours post-dose on Day 1 and 2 hours post-dose on Day 14, Table 8.

Photographic measurement of MRD-1 also showed a positive effect with oxymetazoline hydrochloride treatment. Increases in LPFT were numerically greater in the oxymetazoline hydrochloride group than in the Vehicle group at all post-dosing time points. Greater MRD-1 increases were observed for the oxymetazoline hydrochloride group than the Vehicle group at all post-dosing time points for 6 weeks, Table 9. Increased MRD-1 values observed at 5 minutes post-dose indicated onset of action by 5 minutes.

4.2 Safety

Oxymetazoline hydrochloride was well tolerated, and the AEs that were observed were predominantly mild in intensity.

4.3 Results

Figure 2:
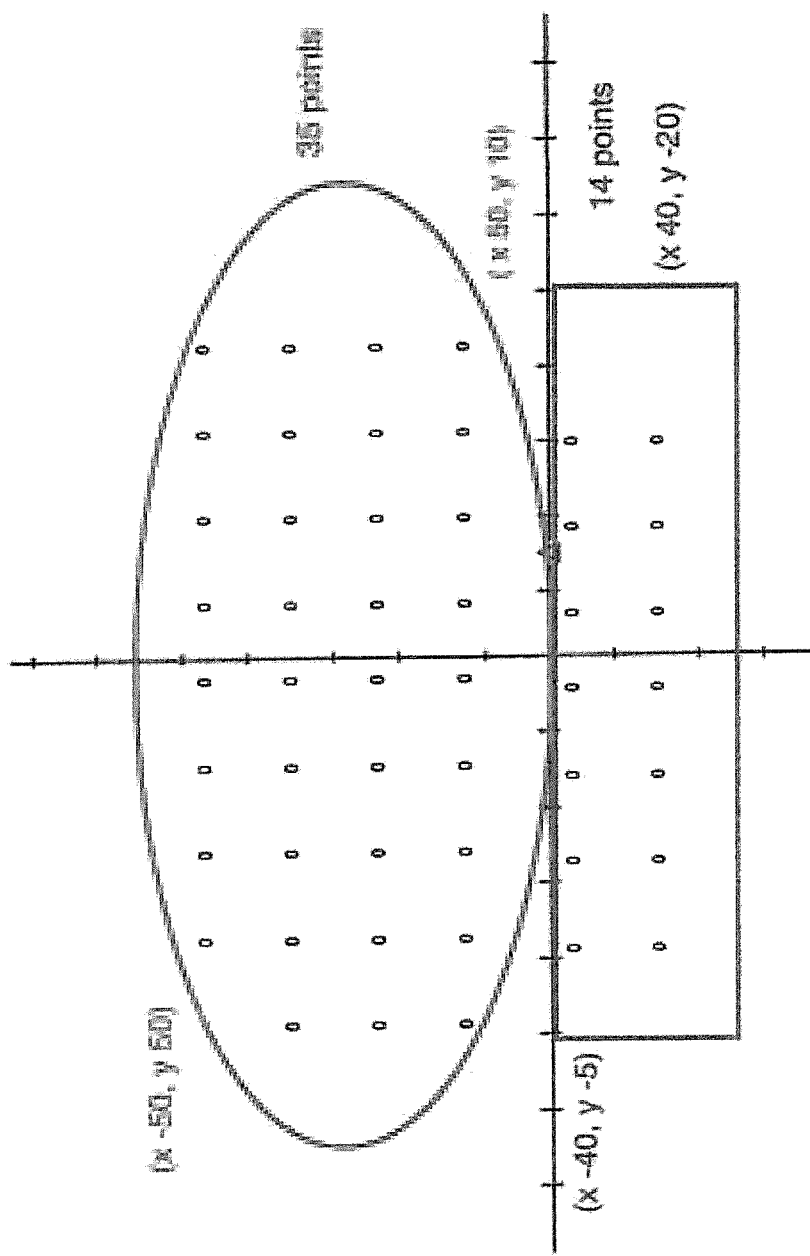
FIG. 2 shows a diagram of the Leicester Peripheral Field Test.

The LPFT was performed using a Humphrey Visual Field Analyzer. It is an age-corrected screening test with a three-zone strategy. Thirty-five points are tested in the superior field while 14 points are tested in the inferior field. A maximum of 48° is tested in the superior visual field. The center of fixation is shifted 15° inferiorly to allow for maximum superior field testing (Ho et al., 2011). The inferior field test serves as a reference but is not used in the analysis. A representative Leicester Peripheral Field Test grid can be seen in FIG. 2. Subjects keep their chin and forehead against the chin and forehead rests, and keep their brows relaxed. Subjects look at the fixation target throughout the test. A corrective lens is not necessary on the LPFT unless the subject would have a difficult time seeing the target without it (e.g., high myope, high hyperope, or high astigmat).

TABLE 8

Observed and Change from Baseline in Mean Points Seen in Superior Visual Field on LPFT in the Study Eye at Primary Efficacy Time Points (ITT Population), Study 2

| Parameter | Points Seen in Superior Visual Field | | Mean Difference, (95% CL), p-value[a] p-value[b] |
|---|---|---|---|
| | Oxymetazoline Hydrochloride N = 109 | Vehicle N = 55 | Oxymetazoline Hydrochloride vs Vehicle |
| Mean points at baseline (SD) | 17.6 (4.92) | 17.6 (5.48) | |
| Mean points at primary efficacy time points | | | |
| Day 1, Hour 6, observed mean (SD) | 23.9 (6.67) | 19.7 (6.16) | |
| Mean change from baseline (SD) | 6.3 (6.72) | 2.1 (4.28) | 4.23 (2.36, 6.09), <0.0001[a] <0.0003[b] |
| Day 14, Hour 2, observed mean (SD) | 25.3 (6.35) | 20.0 (5.84) | |
| Mean change from baseline (SD) | 7.7 (6.41) | 2.4 (5.26) | 5.30 (3.45, 7.14), <0.0001[a] <0.0003[b] |

CL = confidence limit;
ITT = intent-to-treat;
SD = standard deviation
[a] p-value (2-sided t-test) derived from ANCOVA model with treatment as a fixed factor and baseline score as a covariate
[b] p-value (Wilcoxon rank sum test)

Additional data from the above LPFT is detailed below in Table 9:

TABLE 9

Mean Change from Baseline in Marginal Reflex Distance 1 in the Study Eye (ITT Population), Study 2

| Parameter | Oxymetazoline Hydrochloride N = 109 | Vehicle N = 55 | Mean Difference, (95% CL), p-value[a] p-value[b] Oxymetazoline Hydrochloride vs Vehicle |
|---|---|---|---|
| Mean MRD-1 at baseline, mm (SD) | 1.04 (0.735) | 1.07 (0.697) | — |
| Mean change from baseline in MRD-1 at primary efficacy time points, mm (SD) | | | |
| Day 1, 5 minutes | 0.59 (0.721) | 0.20 (0.571) | 0.38, (0.16, 0.59), 0.0007[a] 0.0007[b] |
| Day 1, 15 minutes | 0.93 (0.811) | 0.32 (0.641) | 0.60, (0.36, 0.84), <0.0001[a] <0.0001[b] |

TABLE 9-continued

Mean Change from Baseline in Marginal Reflex Distance 1 in the Study Eye (ITT Population), Study 2

| Parameter | Oxymetazoline Hydrochloride N = 109 | Vehicle N = 55 | Mean Difference, (95% CL), p-value[a] p-value[b] Oxymetazoline Hydrochloride vs Vehicle |
|---|---|---|---|
| Day 1, 2 hours | 1.05 (0.903) | 0.33 (0.555) | 0.71, (0.45, 0.96), <0.0001[a] <0.0001[b] |
| Day 1, 6 hours | 0.98 (0.867) | 0.35 (0.567) | 0.61, (0.37, 0.86), <0.0001[a] <0.0001[b] |
| Day 14, 0 hours | 0.37 (0.805) | 0.40 (0.743) | −0.04, (−0.29, 0.22), 0.7800[a] 0.9648[b] |
| Day 14, 5 minutes | 0.77 (0.853) | 0.42 (0.775) | 0.33, (0.07, 0.60), 0.0151[a] 0.0115[b] |
| Day 14, 15 minutes | 1.11 (0.0.922) | 0.41 (0.833) | 0.68, (0.39, 0.97), <0.0001[a] <0.0001[b] |
| Day 14, 2 hours | 1.22 (0.926) | 0.43 (0.734) | 0.78, (0.50, 1.06), <0.0001[a] <0.0001[b] |
| Day 14, 6 hours | 1.06 (0.902) | 0.47 (0.737) | 0.58, (0.31, 0.85), <0.0001[a] <0.0001[b] |
| Day 42, 5 minutes | 0.86 (0.849) | 0.42 (0.799) | 0.42, (0.15, 0.68), 0.0020[a] 0.0033[b] |
| Day 42, 15 minutes | 1.04 (0.912) | 0.47 (0.926) | 0.55, (0.26, 0.84), 0.0003[a] 0.0005[b] |

CL = confidence limit;
ITT = intent-to-treat;
MRD-1 = marginal reflex distance 1;
SD = standard deviation
[a] p-value (2-sided t-test) derived from ANCOVA model with treatment as a fixed factor and baseline score as a covariate
[b] p-value (Wilcoxon rank sum test)

Example 5

Oxymetazoline HCl Formulation Stability

Stability testing was performed on oxymetazoline hydrochloride preparations across a 24-month span at 40% relative humidity. The results of the stability testing are shown below in Table 10, and vehicle stability data can be found in Table 11.

TABLE 10

Stability Results Every 6 Months at 25° C./40% RH

| Test | Method | Proposed Specification | Time points (Months) | | | | |
|---|---|---|---|---|---|---|---|
| | | | 0 | 6 | 12 | 18 | 24 |
| Appearance | EPS TP-042 | Clear, colorless solution free of any particulates or crystallization | Conforms | Conforms | Conforms | Conforms | Conforms |
| pH | EPS SOP SAS-013 | 5.8-6.8 | 6.5 | 6.4 | 6.5 | 6.5 | 6.4 |
| Osmolality | EPS SOP SAS-005 | 290-330 mOsm/kg | 315 | 304 | 320 | 300 | 318 |
| Viscosity | EPS SOP SAS-057 | 5-25 cps | 24.9 | NT | NT | NT | NT |
| Assay | EPS TP-101 | 90.0-110.0% of Label Claim (1.0 mg/mL) | 99.1% | 96.5% | 95.9% | 95.2% | 93.9% |
| ID by HPLC | EPS TP-101 (USP) | Conforms | Conforms | NT | NT | NT | NT |
| Related Substances | EPS TP-113 | TBD (0.05% reporting Limit) | | | | | |
| | | Unspecified Individual RRT = 0.42 | NT | NT | ND | 0.13% | ND |
| | | Unspecified Individual RRT = 0.50 | NT | NT | 0.46% | 0.73% | 0.13% |
| | | Unspecified Individual RRT = 0.54-0.57 | NT | NT | 0.53% | 0.79% | 0.87% |
| | | Unspecified Individual RRT = 0.61-62 | NT | NT | ND | ND | 0.90 |

TABLE 10-continued

Stability Results Every 6 Months at 25° C./40% RH

| Test | Method | Proposed Specification | 0 | 6 | 12 | 18 | 24 |
|---|---|---|---|---|---|---|---|
| | | Unspecified Individual RRT = 0.81-0.86 | NT | NT | 0.60% | 0.79% | ND |
| | | Unspecified Individual RRT = 1.2 | NT | NT | 0.07% | ND | 1.01% |
| | | Unspecified Individual RRT = 1.9 | NT | NT | 0.09% | 0.10% | 0.10% |
| | | Total Related Substances (Report Results) | NT | NT | 1.68% | 2.61% | 3.07% |
| Particulate Matter | EPS TP-034 microscopic | ≥10 μm NMT 50 per ml | 1 | NT | NT | NT | NT |
| | | ≥25 μm NMT 50 per ml | 0 | NT | NT | NT | NT |
| | | ≥50 μm NMT 50 per ml | 0 | NT | NT | NT | NT |

NT = not tested

TABLE 11

Stability Results Every 6 Months at 25° C./40% RH (Vehicle)

| Test | Method | Proposed Specification | 0 | 6 | 12 | 18 | 24 |
|---|---|---|---|---|---|---|---|
| Appearance | EPS TP-042 | Clear, colorless solution free of any particulates or crystallization | Conforms | Conforms | Conforms | Conforms | Conforms |
| pH | EPS SOP SAS-013 | 5.8-6.8 | 6.5 | 6.2 | 6.4 | 6.4 | 6.5 |
| Osmolality | EPS SOP SAS-005 | 290-330 mOsm/kg | 312 | 306 | 313 | 296 | 311 |
| Viscosity | EPS SOP SAS-057 | 5-25 cps | 18.4 | NT | NT | NT | NT |
| Assay | EPS TP-101 | 90.0-110.0% of Label Claim (1.0 mg/mL) | 0.0% | NT | NT | NT | NT |
| ID by HPLC | EPS TP-101 (USP) | Conforms (none detected) | Conforms | NT | NT | NT | NT |
| Particulate Matter | EPS TP-034 Microscopic | ≥10 μm NMT 50 per ml | 1 | NT | NT | NT | NT |
| | | ≥25 μm NMT 5per ml | 0 | NT | NT | NT | NT |
| | | ≥50 μm NT 2per ml | 0 | NT | NT | NT | NT |

NT = not tested

Oxymetazoline hydrochloride solutions were stable across five time points measured at 0 months, 6 months, 12 months, 18 months, and 24 months, showing good stability and shelf-life for the formulated preparations.

Example 6

Oxymetazoline HCl Clinical Supply Stability Study

Oxymetazoline hydrochloride formulations were prepared according to Table 12. Stability testing was performed on oxymetazoline preparations across a 24- and 30-month span.

TABLE 12

Summary of Batches Used in Clinical Studies, Oxymetazoline Hydrochloride Ophthalmic Solution, 0.1% (RVL-1201)

| Batch number | Active or Vehicle | Batch size | Container/Closure/Fill |
|---|---|---|---|
| 1680614 | Active | 3 L | 1 cc dropperette, 0.7 mL fill |
| 1680615 | Vehicle | 3 L | 1 cc dropperette, 0.7 mL fill |
| RD427 | Active | 150 kg | 0.5 mL BFS in foil pouch, 0.34 mL fill |
| RD425 | Vehicle | 150 kg | 0.5 mL BFS in foil pouch, 0.34 mL fill |
| R80261 | Active | 200 kg | 0.5 mL BFS in foil pouch, 0.34 mL fill |
| R80251 | Vehicle | 200 kg | 0.5 mL BFS in foil pouch, 0.34 mL fill |

Three commercial-scale, one-stage process batches (R60681, R60701, and R60711) were tested at the end of shelf-life, and the results support the proposed 24-month shelf-life. The 24 month and 30-month stability data are presented in FIGS. 3A-3B, 4A-4B, and 5A-5B for each batch (R60681, R60701, and R60711, respectively).

Throughout this application, various publications are referenced in parentheses by author name and date, or by patent No. or patent Publication No. The disclosures of these publications are hereby incorporated in their entireties by reference into this application in order to more fully describe the state of the art as known to those skilled therein as of the date of the disclosure described and claimed herein. However, the citation of a reference herein should not be construed as an acknowledgement that such reference is prior art to the present disclosure.

What is claimed is:

1. A child-resistant packaging having a single use container enclosed therein, wherein the single use container comprises an aqueous ophthalmic, sterile, preservative-free formulation comprising:
    a) about 0.1 wt % oxymetazoline or a pharmaceutically acceptable salt thereof;
    b) sodium chloride, potassium chloride, calcium chloride, and magnesium chloride;
    c) about 0.5 wt % hypromellose;
    d) sodium acetate and sodium citrate;
    e) hydrochloric acid; and
    f) water,
    wherein the formulation has a pH range from about 5.8 to about 6.8;
    wherein the container delivers about 0.035 mg of oxymetazoline or a pharmaceutically acceptable salt thereof per drop; and
    wherein the formulation has a viscosity of about 15 cPs to about 35 cPs.

2. The child-resistant packaging of claim 1, wherein the packaging is a foil pouch.

3. The child-resistant packaging of claim 2, wherein the foil pouch is a foil laminate pouch.

4. The child-resistant packaging of claim 1, wherein the formulation has an osmolality of from about 290 to about 365 mOsm/kg.

5. The child-resistant packaging of claim 1, wherein the container is formed by a blow/fill/seal process.

6. The child-resistant packaging of claim 1, wherein the container is a low density polyethylene container.

7. The child-resistant packaging of claim 1, wherein the pharmaceutically acceptable salt is oxymetazoline hydrochloride.

8. The child-resistant packaging of claim 1, wherein the formulation comprises about 0.64 wt % of sodium chloride, about 0.075 wt % of potassium chloride, about 0.048 wt % of calcium chloride, and about 0.03 wt % of magnesium chloride.

9. The child-resistant packaging of claim 8, wherein the calcium chloride is calcium chloride dihydrate and the magnesium chloride is magnesium chloride hexahydrate.

10. The child-resistant packaging of claim 1, wherein the sodium acetate is sodium acetate trihydrate and the sodium citrate is sodium citrate dihydrate.

11. The child-resistant packaging of claim 1, wherein the formulation comprises about 0.39 wt % sodium acetate and about 0.17 wt % sodium citrate.

12. The child-resistant packaging of claim 1, wherein the formulation has a pH range from about 6.3 to about 6.5.

13. The child-resistant packaging of claim 1, wherein the formulation maintains a pH range from about 5.8 to about 6.8, a viscosity from about 15 cPs to about 35 cPs, and an osmolality from about 290 to about 365 mOsm/kg for a period of 6 months.

14. The child-resistant packaging of claim 1, wherein the formulation is aseptically prepared.

15. A child-resistant foil pouch having a single use low density polyethylene container enclosed therein, wherein the single use container comprises an aqueous ophthalmic, sterile, preservative-free formulation comprising:
    a) about 0.1 wt % oxymetazoline hydrochloride;
    b) sodium chloride, potassium chloride, calcium chloride, and magnesium chloride;
    c) about 0.5 wt % hypromellose;
    d) sodium acetate and sodium citrate;
    e) hydrochloric acid; and
    f) water,
    wherein the formulation has a pH range from about 5.8 to about 6.8,
    wherein the formulation has a viscosity of from about 15 cPs to about 35 cPs,
    wherein the formulation has an osmolality of from about 290 to about 365 mOsm/kg, and
    wherein the container delivers about 0.035 mg of oxymetazoline or a pharmaceutically acceptable salt thereof per drop.

16. The child-resistant foil pouch of claim 15, wherein the foil pouch is a foil laminate pouch.

17. The child-resistant foil pouch of claim 15, wherein the fill of the container is about 0.3 mL.

18. The child-resistant foil pouch of claim 15, wherein volume of the container is about 0.5 mL.

19. The child-resistant foil pouch of claim 15, wherein the container is formed by a blow/fill/seal process.

20. The child-resistant foil pouch of claim 15, wherein the formulation comprises about 0.64 wt % of sodium chloride, about 0.075 wt % of potassium chloride, about 0.048 wt % of calcium chloride or calcium chloride dihydrate, and about 0.03 wt % of magnesium chloride or magnesium chloride hexahydrate.

21. The child-resistant foil pouch of claim 15, wherein the sodium acetate is sodium acetate trihydrate and the sodium citrate is sodium citrate dihydrate.

22. The child-resistant foil pouch of claim 15, wherein the formulation comprises about 0.39 wt % sodium acetate and about 0.17 wt % sodium citrate.

23. The child-resistant foil pouch of claim 15, wherein the formulation maintains a pH range from about 5.8 to about 6.8, a viscosity from about 15 cPs to about 35 cPs, and an osmolality from about 290 to about 365 mOsm/kg for a period of 6 months.

24. The child-resistant packaging of claim 13, wherein the formulation maintains the pH range, the viscosity range and the osmolality range for a period of 12 months.

25. The child-resistant packaging of claim 13, wherein the formulation maintains the pH range, the viscosity range and the osmolality range for a period of 18 months.

26. The child-resistant packaging of claim 13, wherein the formulation maintains the pH range, the viscosity range and the osmolality range at a temperature of about 25° C. and about 60% relative humidity.

27. The child-resistant foil pouch of claim 23, wherein the formulation maintains the pH range, the viscosity range and the osmolality range for a period of 12 months.

28. The child-resistant foil pouch of claim 23, wherein the formulation maintains the pH range, the viscosity range and the osmolality range for a period of 18 months.

29. The child-resistant foil pouch of claim 23, wherein the formulation maintains the pH range, the viscosity range and the osmolality range at a temperature of about 25° C. and about 60% relative humidity.

* * * * *